United States Patent
Xu et al.

(10) Patent No.: US 7,455,983 B2
(45) Date of Patent: Nov. 25, 2008

(54) MEDIUM FOR GROWING HUMAN EMBRYONIC STEM CELLS

(75) Inventors: Chunhui Xu, Palo Alto, CA (US); Yan Li, Menlo Park, CA (US); Ramkumar Mandalam, Union City, CA (US)

(73) Assignee: Geron Corporation, Menlo Park, CA (US)

( * ) Notice: Subject to any disclaimer, the term of this patent is extended or adjusted under 35 U.S.C. 154(b) by 179 days.

(21) Appl. No.: 10/949,181

(22) Filed: Sep. 24, 2004

(65) Prior Publication Data

US 2005/0037492 A1    Feb. 17, 2005

Related U.S. Application Data

(63) Continuation-in-part of application No. 10/235,094, filed on Sep. 4, 2002, now Pat. No. 7,410,798, application No. 10/949,181, which is a continuation-in-part of application No. PCT/US01/01030, filed on Jan. 10, 2001.

(60) Provisional application No. 60/587,843, filed on Jul. 13, 2004, provisional application No. 60/317,478, filed on Sep. 5, 2001, provisional application No. 60/220,064, filed on Jul. 21, 2000, provisional application No. 60/216,387, filed on Jul. 7, 2000, provisional application No. 60/213,739, filed on Jun. 22, 2000, provisional application No. 60/213,740, filed on Jun. 22, 2000, provisional application No. 60/175,581, filed on Jan. 11, 2000.

(51) Int. Cl.
G01N 33/53    (2006.01)
C12N 1/00    (2006.01)
C12N 5/383    (2006.01)

(52) U.S. Cl. .......................... 435/7.21; 435/4; 435/366; 435/377; 435/383; 435/385

(58) Field of Classification Search ...................... 435/4, 435/7.21, 366, 377, 383, 385
See application file for complete search history.

(56) References Cited

U.S. PATENT DOCUMENTS

| | | | |
|---|---|---|---|
| 5,104,795 A | 4/1992 | Lee et al. | 435/69.1 |
| 5,166,065 A | 11/1992 | Williams et al. | 435/240.1 |
| 5,234,809 A | 8/1993 | Boom et al. | 435/91 |
| 5,332,672 A | 7/1994 | Conover et al. | 435/240.2 |
| 5,405,772 A | 4/1995 | Ponting | 435/240.31 |
| 5,453,357 A | 9/1995 | Hogan | 435/7.21 |
| 5,464,764 A | 11/1995 | Capecchi et al. | 435/172.3 |
| 5,523,226 A | 6/1996 | Wheeler | 435/240.2 |
| 5,583,016 A | 12/1996 | Villeponteau et al. | 435/91.3 |
| 5,591,625 A | 1/1997 | Gerson et al. | 435/240.2 |
| 5,639,618 A | 6/1997 | Gay | 435/7.21 |
| 5,643,761 A | 7/1997 | Fisher et al. | 435/91.1 |
| 5,672,499 A | 9/1997 | Anderson et al. | 435/240.4 |
| 5,789,158 A | 8/1998 | Knowles et al. | 435/6 |
| 5,840,484 A | 11/1998 | Seilhamer et al. | 435/6 |
| 5,843,780 A | 12/1998 | Thomson | 435/363 |
| 5,856,136 A | 1/1999 | Au-Young | 435/69.3 |
| 5,914,268 A | 6/1999 | Keller et al. | 435/325 |
| 5,922,597 A | 7/1999 | Verfaillie et al. | 435/372.1 |
| 5,942,435 A | 8/1999 | Wheeler | 435/325 |
| 5,968,829 A | 10/1999 | Carpenter | 435/467 |
| 5,981,165 A | 11/1999 | Weiss et al. | 435/4 |
| 6,040,180 A | 3/2000 | Johe | 435/377 |
| 6,200,806 B1 | 3/2001 | Thomson | 435/366 |
| 6,261,556 B1 | 7/2001 | Weinrich et al. | 424/94.5 |
| 6,800,480 B1 | 10/2004 | Bodnar et al. | |
| 6,875,607 B1 | 4/2005 | Reubinoff et al. | 435/325 |
| 7,005,252 B1 | 2/2006 | Thomson | |
| 2005/0148070 A1 | 7/2005 | Thomson et al. | 435/366 |

FOREIGN PATENT DOCUMENTS

| | | |
|---|---|---|
| AU | 729377 B | 2/2001 |
| EP | 0695 351 B1 | 12/1999 |
| FR | 2744133 A1 | 8/1997 |
| WO | WO 94/07997 | 4/1994 |
| WO | WO 96/17627 | 6/1996 |

(Continued)

OTHER PUBLICATIONS

Lim et al. Proteomics, 2:1187-1203, 2002.*
Akiyama, H., et al, Molecular Cloning and Biological Activity of a Novel Ha-Ras Suppressor Gene Predominantly Expressed in Skeletal Muscle, Heart, Brain, and Bone Marrow by Differential Display Using Clonal Mouse EC Cells, ATDC5, J Biological Chemistry 274(45):32192 (1999).
Amit, M., et al., "Clonally Derived Human Embryonic Stem Cell Lines Maintain Pluripotency and Proliferative Potential for Prolonged Periods of Culture," Dev. Biol., 227:271 (2000).
Amit, M., et al., "Human feeder layers for human embryonic stem cells," Biol. Reprod., 68:2150 (2003).
Amit, M., et al., "Feeder layer- and serum-free culture of human embryonic stem cells," Biol. Reprod., 70:837 (2004).

(Continued)

*Primary Examiner*—Thaian N Ton
(74) *Attorney, Agent, or Firm*—E. Stewart Mittler

(57) ABSTRACT

This disclosure provides an improved system for culturing human pluripotent stem cells. Traditionally, pluripotent stem cells are cultured on a layer of mouse embryonic fibroblast feeder cells to prevent them from differentiating. In the system described here, the role of feeder cells is replaced by defined components added to the culture environment that support rapid proliferation without differentiation. The medium contains an isotonic buffer, a blend of essential nutrients such as protein and lipids, and an effective growth factor or combination of factors that promote proliferation while inhibiting differentiation. Culturing human embryonic stem cells in fresh medium on an extracellular matrix according to this invention causes the cells to expand surprisingly rapidly, while retaining the ability to differentiate into cells representing all three embryonic germ layers. This new culture system allows for bulk proliferation of pPS cells for commercial production of important products for use in drug screening and human therapy.

1 Claim, 11 Drawing Sheets

FOREIGN PATENT DOCUMENTS

| WO | WO 97/21802 | 6/1997 |
| WO | WO 97/28253 | 8/1997 |
| WO | WO 97/30151 | 8/1997 |
| WO | WO 97/47734 | 12/1997 |
| WO | WO 98/00540 | 1/1998 |
| WO | WO 98/30678 | 7/1998 |
| WO | WO 98/30679 | 7/1998 |
| WO | WO 98/43679 | 10/1998 |
| WO | WO 99/01552 | 1/1999 |
| WO | WO 99/10535 | 3/1999 |
| WO | WO 99/20741 | 4/1999 |
| WO | WO 99/42122 | 8/1999 |
| WO | WO 99/43785 | 9/1999 |
| WO | WO 01/51616 A2 | 7/2001 |
| WO | WO 01/66697 A2 | 9/2001 |

OTHER PUBLICATIONS

Andrews, P., "Retinoic Acid Induces Neuronal Differentiation of a Cloned Human Embryonal Carcinoma Cell Line in Vitro," Dev. Biol., 103:285 (1984).

Aouadi, M., et al., "P38MAPK activity commits embryonic stem cells to either neurogenesis or cardiomyogenesis," Stem Cells Express, published online Jan. 19, 2006, doi:10.1634/stemcells.2005-0398.

Baribault, H., et al., "Embryonic Stem Cell Culture and Gene Targeting in Transgenic Mice," Mol. Biol. Med. 6:481 (1989).

Beattie, G., et al., "Activin A maintains pluripotency of human embryonic stem cells in the absence of feeder layers," Stem Cells, 23:489 (2005).

Berger, C., et al., "Self Renewal of Embryonic Stem Cells in the Absence of Feeder Cells and Exogenous Leukaemia Inhibitory Factor," Growth Factors, 14:145 (1997).

Bodnar, A., et al., "Extension of Life-Span by Introduction of Telomerase into Normal Human Cells," Science, 279:349 (1998).

Bongso, A., et al., "Improved Quality of Human Embryos When Co-Cultured with Human Ampullary Cells," Hum. Reprod., 4:706 (1989).

Bradley, A., et al., "Modifying the Mouse: Design and Desire," Biotechnology, 10:534 (1992).

Brook, F., et al., "The Origin and Efficient Dirivation of Embryonic Stem Cells in the Mouse," Proc. Natl. Acad. Sci., 94:5709 (1997).

Carnegie, J., "Immonolocalization of Fibronectin and Laminin Within Rat Blastocysts Cultured Under Serum-Free Conditions," J. Reprod. Fert., 91:423 (1991).

Carninci, P., et al., "High-Efficiency Full-Length cDNA Cloning," Methods Enzymol., 303:19 (1999).

Carpenter, M., et al., "Properties of four human embryonic stem cell lines maintained in a feeder-free culture system", Dev. Dyn., 229:243 (2004).

Cheng L., et al., "Human adult marrow cells support prolonged expansion of human embryonic stem cells in culture," Stem Cells, 21:131 (2003).

Corrick, C., et al., "Construction of a Mouse Blastocyst cDNA Library by PCR Amplification From Total RNA," Molecular Reproduction and Development, 43:7 (1996).

Deleersnijder, W., et al., "Isolation of markers for chondro-osteogenic differentiation using cDNA library subtraction. Molecular cloning and characterization of a gene belonging to a novel multigene family of integral membrane proteins", J Biol Chem, 271:19475 (1996).

Denning, C., et al., "Common culture conditions for maintenance and cardiomyocyte differentiation of the human embryonic stem cell lines, BG01 and HUES-7," Int. J. Dev. Biol., 50:27 (2006).

Dravid, G., et al., "Defining the role of Wnt-catenin signaling in the survival, proliferation and self-renewal of human embryonic stem cells," Stem Cells, 23(10):1489 (2005).

Dvorak, P., et al., "Expression and potential role of fibroblast growth factor 2 and its receptors in human embryonic stem cells," Stem Cells, 23:1200 (2005).

Elsen, M., "Cluster Analysis and Display of Genome-wide Expression Patturns," Proc. Natl. Acad. Sci., 95:14868 (1998).

Elges, R., et al., "Establishment of Human Embryonic Stem Cell-Transfected Clones Carrying a Marker for Undifferentiated Cells," Curr Biol, 11:514 (2001).

Evans, M., et al., "Establishment in Culture of Pluripotential Cell from Mouse Embryos," Nature, 292:154 (1981).

Fabb S., et al., "High-efficiency human B-cell cloning using hygromycin B-resistant feeder cells," Biotechniques, 22(5):814 (1997).

Fenderson, B., et al., "Carbohydrate Antigens of Embryonal Carcinoma Cells: Changes Upon Differentiation," APMIS Suppl. 27, 100:109 (1992).

Finley, M., et al., "Synapse Formation and Establishment of Neuronal Polarity by P19 Embryonic Carcinoma Cells and Embryonic Stem Cells," J. Neuroscience, 16:1056 (1996).

Gardner, D., et al., "Culture and Transfer of Human Blastocysts Increases Implantation Rates and Reduces the Need for Multiple Embryo Transfers," Fertil. Steril, 69:84 (1998).

Genbacev, O., et al., "Serum-free derivation of human embryonic stem cell lines on human placental fibroblast feeders," Reprod. Biol., 83(5):1517 (2005).

Gendall, A., et al., "Isolation and Characterization of a Leukemia Inhibitory Factor-Independent Embryonic Stem Cell Line," Int. J. Biochem Cell Biol., 29:829 (1997).

Gendron, R., et al., "Induction of Embryonic Vasculogenesis by bFGF and LIF in Vitro and in Vivo," Developmental Biology, 177:332 (1996).

Herszfeld, D., et al., "CD30 is a survival facto and biomarker for transformed human plurpotent stem cells," Nature Biol.

Hovatta, O., et al., "A culture system using human foreskin fibroblasts as feeder cells allows production of human embryonic stem cells," Hum Reprod., 18:1404 (2003).

Itoh, M., et al., "Automated Filtration-Based High-Throughput Plasmid Preparation System," Genome Res., 9:463 (1999).

Itskovitz-Eldor, J., et al., "Differentiation of Human Embryonic Stem Cells into Embrynoid Bodies Comprising the Three Embryonic Germ Layers," Mol. Med., 6:88 (2000).

James, D., et al., "TGF□/activin/nodal signaling is necessary for the maintenance of pluripotency in human embryonic stem cells," Development, 132(6):1273 (2005).

Johnson KA et al., Transgenic Mice for the Preparation of Hygromcyin-Resistant Primary Embryonic Fibroblast Feeder Layers for Embryonic Stem Cell Selections, Nucleic Acids Research 23(7):1273 (1995).

Keller, G., "In Vitro Differentiation of Embryonic Stem Cells," Cell Biology, 7:862 (1995).

Kelly, DL., et al., "DNA Microarray Analyses of Genes Regulated During the Differentiation of Embryonic Stem Cells," Mol Reprod. Dev., 56:113 (2000).

Ko, M., et al., "Large-scale cDNA analysis Reveals Phased Gene Expression Patterns During Preimplantation Mouse Development," Development, 127:1737 (2000).

Koshimizu, U., et al., "Functional Requirement of gp130-mediated Signaling for Growth and Survival of Mouse Primordial Germ Cells in Vitro and Derivation of Embryonic Germ (EG) Cells," Development, 122:1235 (1996).

Koshimizu, U., et al., "Rapid Communication Retinoic Acid Is a Potent Growth Activator of Mouse Primordial Germ Cells in Vitro," Developmental Biology, 168:683 (1995).

Levenstein, M., et al., "Basic FGF support of human embryonic stem cell self-renewal," Stem Cells Express, publised online Nov. 10, 2005; dol:10.1634/stemcells.2005-0247.

Li, Y., et al., "Expansion of human embryonic stem cells in defined serum-free medium devoid of animal-derived products," Biotechnol. Bioeng., 91(6):688-98 (2005).

Ludwig, T., et al., "Derivation of human embryonic stem cells in defined conditions," Nat. Biotech., 24(2):185 (2006).

Matsuda, T., et al., "STAT3 Activation is Sufficient to Maintain an Undifferentiated State of Mouse Embryonic Stem Cells," EMBO J., 18:4261 (1999).

Matsui, Y., et al., "Derivation of Pluripotential Embryonic Stem Cells from Murine Primordial Germ Cells in Culture," Cell, 70:841 (1992).

Miyamoto K., et al., "Human placenta feeder layers support undifferentiated growth of primate embryonic stem cells," Stem Cells., 22:433 (2004).

Nichols, J., et al., "Establishment of Germ-line-Competent Embryonic Stem (ES) Cells Using Differentiation Inhibiting Activity," Development, 110:1341 (1990).

Nichols, J., et al., "Derivation of Germline Competent Embryonic Stem Cells with a Combination of Interleukin-6 and Soluble Interleukin-6 Receptor," Experimental Cell Research, 215:237 (1994).

O'Shea, K., "Embryonic Stem Cell Models of Development," New Anat., 257:32 (1999).

Pease, S., et al., "Isolation of Embryonic Stem (ES) Cells in Media Supplemented with Recombinant Leukemia Inhibitory Factor (LIF)," Developmental Biology, 141:344 (1990).

Pebay, A., et al., "Essential roles of sphingosine-1-phosphate and platelet-derived growth factor in the maintenance of human embryonic stem cells," Stem Cells, 23(10):1541 (2005).

Pera, M., "Human Pluripotent Stem Cells: a Progress Report," Curr Opin Genet Dev, 11:595 (2001).

Pedersen, R., "Studies of In Vitro Differentiation with Embryonic Stem Cells," Reprod. Fertil. Dev., 6:543 (1994).

Pedersen, R., "Embryonic Stem Cell for Medicine," Scientif. Am., 280:68 (1999).

Pyle, A. D., et al., "Neurotrophins mediate human embryonic stem cell survival," Nature Bio., 24(3):344 (2006).

Rathjen, J., et al., "Formation of a Primitive Ectoderm Like Cell Population, EPL Cells, from ES Cells in Response to Biologically Derived Factors," J. of Cell Sci., 112:601 (1999).

Rehman, N., et al., "Development of IVM-IVF Produced 8-Cell Bovine Embryons in Simple, Serum-Free Media After Conditioning or Co-Culture With Buffalo Rat Liver Cells," Mol. Repro. Dev, 38:251 (1994).

Reubinoff, B., et al., "Embryonic Stem Cell Lines From Human Blastocysts: Somatic Differentiation In Vitro," Nat. Biotechnology, 18:399 (2000).

Richards M., et al., "Comparative evaluation of various human feeders for prolonged undifferentiated growth of human embryonic stem cells" Stem Cells 21:546 (2003).

Richards, M., et al., Human feeders support prolonged undifferentiated growth of human inner cell masses and embryonic stem cells, Nat Biotechnol., 20:933 (2002).

Robertson, E., "Derivation and Maintenance of Embryonic Stem Cell Cultures," Methods in Mol. Bio., 75:173 (1997).

Rose, T., et al., "Oncostatin M (OSM) Inhibits the Differentiation of Pluripotent Embryonic Stem Cells In Vitro," Cytokine, 6:48 (1994).

Rosler, E., et al., Long-term culture of human embryonic stem cells in feeder-free conditions, Dev. Dyn., 229:259 (2004).

Sato, N., et al., "Maintenance of pluripotency in human and mouse embryonic stem cells through activation of Wnt signaling by a pharmalogical GSK-3-specific inhibitor," Nat. Med., 10(1):55 (2004).

Sato N, et al., "Molecular signature of human embryonic stem cells and its comparison with the mouse. Dev Biol." 260:404 (2003).

Shamblott, M., et al., "Human Embryonic Germ Cell Derivatives Express a Broad Range of Developmentally Distinct Markers and Proliferate Extensively in Vitro," PNAS, 98: 113 (2001).

Shamblott, M., et al., "Derivation of Pluripotent Stem Cells from Cultured Human Primordial Germ Cells," Proc. Natl. Acad. Sci. USA, 95:13726 (1998).

Simon C., et al., "First derivation in Spain of Human embryonic stem cell lines: use of long-term cryopreserved embryos and animal-free conditions," Fertil Steril. 83:246 (2005).

Smith, A., et al., "Inhibition of Pluripotential Embryonic Stem Cell Differentiation by Purified Polypeptides," Nature, 336:668 (1998).

Smith, A., et al., "Buffalo Rat Liver Cells Produce a Diffusable Activity Which Inhibits the Differntiation of Murine Embryonal Carcinoma and Embryonic Stem Cells," Dev. Biol., 121:1 (1987).

Stojkovic P., et al., "An autogeneic feeder cell system that efficiently supports growth of undifferentiated human embryonic stem cells," Stem Cells. 23:306 (2005).

Takahashi, N., et al., "Toward a Whole cDNA Catalog: Construction of an Equalized cDNA library from Mouse Embryos," Genomics, 23:202 (1994).

Thomson, J., et al., "Embryonic Stem Cell Lines Derived from Human Blastocysts," Science, 282:1145 (1998).

Thomson, J., et al., "Neural Differentiation of Rhesus Embryonic Stem Cells," APMIS, 106:149 (1998).

Thomson, J., et al., "Isolation of a Primate Embryonic Stem Cell Line," Proc. Natl. Acad. Sci. USA, 92:7844 (1995).

Thomson, J., et al., "Primate Embryonic Stem Cells," Current Topics in Developmental Biology, 38:133 (1998).

Tucker RM et al, Transgenic Mice for the Establishment of Histidinol-Resistant Embryonic Fibroblast Feeder Layers, FASEB J 10:1641 (1996).

Vallier, L., et al., "Nodal Inhibits differentiation of human embryonic stem cells along the neuroectodermal default pathway," Dev. Biol., 275:403 (2004)

Vallier, L., et al., "Activin/Nodal and FGF pathways cooperate to maintain pluripotency of human embryonic stem cells," J. Cell Sci., 118:4495 (2005).

Vassilieva, S., et al., "Establishment of SSEA-1- and Oct-4-Expressing Rat Embryonic Stem-like Cell Lines and Effects of Cytokines of the IL-6 Family on Clonal Growth," Exper. Cell Research, 258:361 (2000).

Wang G, et al., "Noggin and bFGF cooperate to maintain the pluripotency of human embryonic stem cells in the absence of feeder layers. Biochem Biophys Res Commun," 330:934 (2005).

Wang, L., et al., "Human embryonic stem cells maintained in the absence of mouse embryonic fibroblasts or conditioned media are capable of hematopoietic development," Blood, 105(12):4598 (2005).

Wang Q., et al., "Derivation and Growing Human Embryonic Stem Cells on Feeders," Stem Cells. 23(9):1221(2005).

Wenk, J., et al., "Glycolipids of Germ Cell Tumors: Extended Globo-Series Glycolipids are a Hallmark of Human Embryonal Carcinoma Cells," Int. J. Cancer, 58:108 (1994).

Williams, R., et al., "Myeloid Leukaemia Inhibitory Factor Maintains the Developmental Potential of Embryonic Stem Cells," Nature, 336:684 (1988).

Woltjen, K., et al., "Retro-recombination Screening of a Mouse Embryonic Stem Cell Genomic Library," Nucleic Acids Research, 28:e41 (2000).

Xiong, J., et al., "Large-Scall Screening for Developmental Genes in Embryonic Stem Cells and Embryoid Bodies Using Retroviral Entrapment Vectors," Dev. Dynamics, 212:181 (1998).

Xu, C., et al., "Feeder-free growth of undifferentiated human embryonic stem cells," Nat. Biotech, 19:971 (2001).

Xu, C., et al., "Basic fibroblast growth factor supports undifferentiated human embryonic stem cell growth without conditioned medium," Stem Cells, 23:315 (2005).

Xu C., et al., "Immortalized fibroblast-like cells derived from human embryonic stem cells support undifferentiated cell growth," Stem Cells, 22:972 (2004).

Xu, R., et al., "Basic FGF and suppression of BMP signaling sustain undifferentiated proliferation of human ES cells," Nat. Methods, 2(3):185 (2005).

Zandstra, P., et al., "Leukenia Inhibitory Factor (LIF) Concentration Modulates Embryonic Stem Cell Self-Renewal and Differentiation Independently of Proliferation," Biotechnol. Bioeng., 69:607 (2000).

Anzai, H. et al., "Self-renewal and differentiation of a basic fibroblast growth factor-dependent multipotent hematopoietic cell line derived from embryonic stem cells," *Develop. Growth Differ.* 41:51-8 (1999).

Klimanskaya, I. et al., "Human embryonic stem cells derived without feeder cells," *Lancet* 365(9471):1636-41 (2005).

Kuang, W. et al., "Disruption of the *lama2* gene in embryonic stem cells: Laminin α2 is necessary for sustenance of mature muscle cells," *Exp. Cell Res.* 241:117-25 (1998).

Lebkowski, J. et al., "Human embryonic stem cells: culture, differentiation, and genetic modification for regenerative medicine applications," *Cancer J.* 7(Suppl 2):S83-S94 (2001).

Sciaky, D. et al., "Cultured human fibroblasts express constitutive IL-16 mRNA: cytokine induction of active IL-16 protein synthesis through a caspase-3-dependent mechanism," *J. Immunol.* 164:3806-14 (2000).

Worrall, D. et al., "A carrot leucine-rich-repeat protein that inhibits ice recrystallization," *Science* 282:115-7 (1998).

Zhang, S-C. et al., "In vitro differentiation of transplantable neural precursors from human embryonic stem cells," *Nature Biotech* 19:1129-33 (2001).

* cited by examiner

MEDIUM FOR GROWING HUMAN EMBRYONIC STEM CELLS

REFERENCE TO RELATED APPLICATIONS

This application claims the priority benefit of U.S. provisional patent appliaction U.S. Ser. No. 60/587,843, filed Jul. 13, 2004.

This application is a continuation-in-part of U.S. patent application Ser. No. 10/235,094, filed Sep. 4, 2002 now U.S. Pat. No. 7,410,798, through which it claims the priority benefit of U.S. provisional patent application U.S. Ser. No. 60/317,478, filed Sep. 5, 2001.

This application is also a continuation-in-part of PCT application PCT/US01/01030, filed Jan. 10, 2001, designating the U.S., and published as WO 01/51616 on Jul. 19, 2001; which claims priority to U.S. Ser. No. 60/175,581, filed Jan. 11, 2000; U.S. Ser. No. 60/213,740, filed Jun. 22, 2000; U.S. Ser. No. 60/213,739, filed Jun. 22, 2000; U.S. Ser. No. 60/216,387, filed Jul. 7, 2000; U.S. Ser. No. 60/220,064, filed Jul. 21, 2000; U.S. Ser. No. 09/688,031, filed Oct. 10, 2000 (now U.S. Pat. No. 6,667,176); U.S. Ser. No. 09/849,022, filed May 4, 2001 (pending); U.S. Ser. No. 09/888,309, filed Jun. 21, 2001 (pending); and U.S. Ser. No. 09/900,752, filed Jul. 6, 2001 (now U.S. Pat. No. 6,642,048).

The priority applications are hereby incorporated herein by reference in their entirety, along with WO 99/20741 and WO 03/020920, with respect to the derivation, culturing, and use of undifferentiated embryonic stem cells and their equivalents. Also incorporated herein by reference are PCT applications WO 01/81549; WO 01/88104; WO 03/000868; WO 03/004605; WO 03/006950; WO 03/050251; WO 03/050249; WO 03/050250; and WO 2004/007696 with respect to the differentiation of hES cells into other cell types; and published U.S. Patent Application US 2003/0224411 A1 with respect to markers useful for characterizing hES cell cultures.

BACKGROUND

Regenerative medicine is benefiting from recent advances relating to the isolation, culture, and use of various types of progenitor cells. This disclosure provides further improvements for the commercial development of human pluripotent stem cells and their derivatives.

Embryonic stem cells have two very special properties: First, unlike other normal mammalian cell types, they can be propagated in culture almost indefinitely, providing a virtually unlimited supply. Second, they can be used to generate a variety of tissue types of interest as a source of replacement cells and tissues for use in tissue therapy, or for use in the screening of pharmaceutical agents.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090,622). Both hES and hEG cells have the long-sought characteristics of pluripotent stem cells: they can be cultured extensively without differentiating, they have a normal karyotype, and they are capable of producing a number of important cell types.

A significant challenge to the use of pluripotent stem cells for therapy is that they are traditionally cultured on a layer of feeder cells to prevent differentiation (U.S. Pat. Nos. 5,843,780; 6,090,622). According to Thomson et al. (Science 282: 114, 1998), hPS cells cultured without feeders soon die, or differentiate into a heterogeneous population of committed cells. Leukemia inhibitory factor (LIF) inhibits differentiation of mouse ES cells, but it does not replace the role of feeder cells in preventing differentiation of human ES cells.

International Patent Publication WO 99/20741 (Geron Corp.) is entitled *Methods and materials for the growth of primate-derived primordial stem cells*. International Patent Publication WO 01/51616 (Geron Corp.) is entitled *Techniques for growth and differentiation of human pluripotent stem cells*. An article by Xu et al. (Nature Biotechnology 19:971, 2001) is entitled *Feeder-free growth of undifferentiated human embryonic stem cells*. An article by Lebkowski et al. (Cancer J. 7 Suppl. 2:S83, 2001) is entitled *Human embryonic stem cells: culture, differentiation, and genetic modification for regenerative medicine applications*. These publications report exemplary culture reagents and techniques for propagating embryonic stem cells in an undifferentiated state, and their use in preparing cells for human therapy.

The new technology described in this disclosure will facilitate growing and manipulating undifferentiated pluripotent stem cells, and help realize the full commercial potential of embryonic cell therapy.

SUMMARY OF THE INVENTION

This disclosure provides an improved system for culturing and proliferating primate pluripotent stem (pPS) cells. The technology allows the user to rapidly produce high-quality embryonic stem cells for use in therapy and drug discovery, in a cost-effective and controlled manner, from defined or commercially available reagents.

Application of the technology involves introducing stem cells into a culture environment containing components described and exemplified in more detail in the sections that follow. Typically, the environment will contain a support structure such as an extracellular matrix, a culture medium, and one or more factors added to the medium that support proliferation of the pPS cells in an undifferentiated state.

Exemplary culture media comprise an isotonic buffer, a protein or amino acid source, and may also comprise nucleotides, lipids, and hormones. An exemplary factor for including in the medium is a fibroblast growth factor. It has been discovered that high concentration FGF in a suitable medium is sufficient to maintain pPS cells in a substantially undifferentiated state through extended culture. Other factors listed in this disclosure can be added to improve the quality and expansion rate of the culture when desired. The media may be made from defined components, wherein all protein in the medium is human. This means that each protein is either isolated from a human tissue or fluid, or has been recombinantly produced by expressing a suitably adapted human gene sequence.

One aspect of this invention is a system of reagents and techniques suitable for commercial distribution that can be used for culturing pPS cells in vitro such that they proliferate without differentiating. One such product or component is a tissue culture medium (either ready for culture, or in concentrated, powdered, or component form that are diluted or combined prior to culture). Medium components typically include an isotonic buffer, protein nutrient, lipids, and growth factors, exemplified by a high concentration of fibroblast growth factor (FGF). Other possible ingredients are listed in the Detailed Description and Examples.

The system may also comprise an extracellular matrix, designed for supporting pPS cell culture in combination with a medium according to this invention. The system may also comprise tissue culture vessels and reagents to monitor and characterize the cells during culture. The reagent system of this invention may be distributed separately, or in conjunction with pPS cells of an established cell line.

It is often helpful to distribute the medium and other components of this invention with written information for the use of the materials for culturing or expanding pPS cells according to this disclosure.

Further embodiments of the invention include the combined composition of the culture environment and the pPS cells, and various methods for expanding pPS cells using the reagents and techniques described in this disclosure. The undifferentiated pPS cells can then act as a reservoir for generating differentiated populations of cells for use in therapy, drug screening, and for other useful purposes.

These and other aspects of the invention will be apparent from the description that follows.

DRAWINGS

FIG. 1 shows hES cells maintained for 6 passages in medium conditioned by mouse embryonic fibroblasts (mEF-CM), fresh SR medium alone, or fresh medium supplemented with 40 ng/mL bFGF or bFGF with stem cell factor bar=800 μm. The presence of bFGF at 40 ng/mL in fresh medium was sufficient to maintain the undifferentiated phenotype in a manner comparable to conditioned medium. Cells grown in fresh SR medium unsupplemented with FGF showed substantial differentiation.

FIG. 2 shows that a high proportion of cells grown in fresh medium maintain the undifferentiated phenotype, as measured by high-level expression of SSEA-4 and Tra-1-81.

FIG. 3 compares SSEA-4 and Tra-1-81 expression amongst different growth conditions Media containing high FGF (marked by "+") maintained the undifferentiated phenotype comparable to cells grown in mEF conditioned medium; whereas combinations of growth factors without FGF (marked by "−") showed evidence of differentiation.

Figure 6:
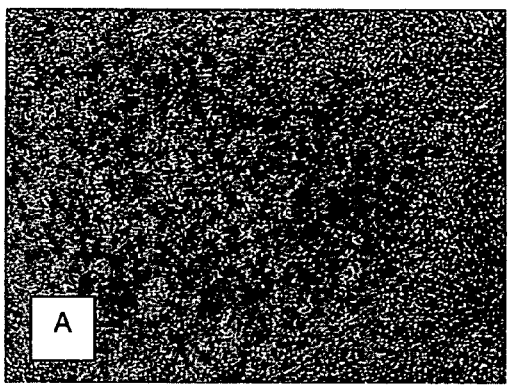
Figure 6:
Figure 6:
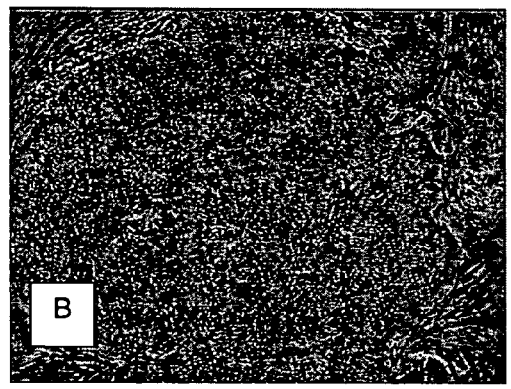
Figure 6:
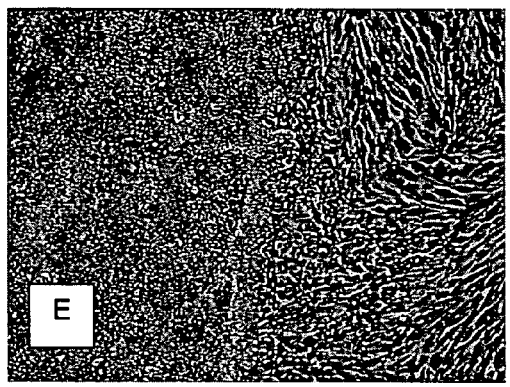
Figure 6:
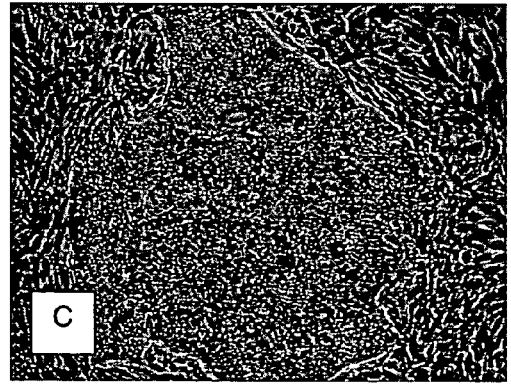

FIG. 6 shows colonies of hES cells after six passages (sufficient for full adaptation) in different base media. (A) mEF conditioned ES medium+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™–60+bFGF (40 ng/mL). All three base media (ES medium, X-VIVO™ 10, and QBSF™–60) can be used to expand hES cells in feeder-free culture. In this illustration, the cells growing in combination shown in (C) expanded 8.2-fold per passage, whereas those in conditioned medium expanded 2.2-fold. The use of suitable fresh medium causes rapid expansion of undifferentiated hES cells.

Figure 7:
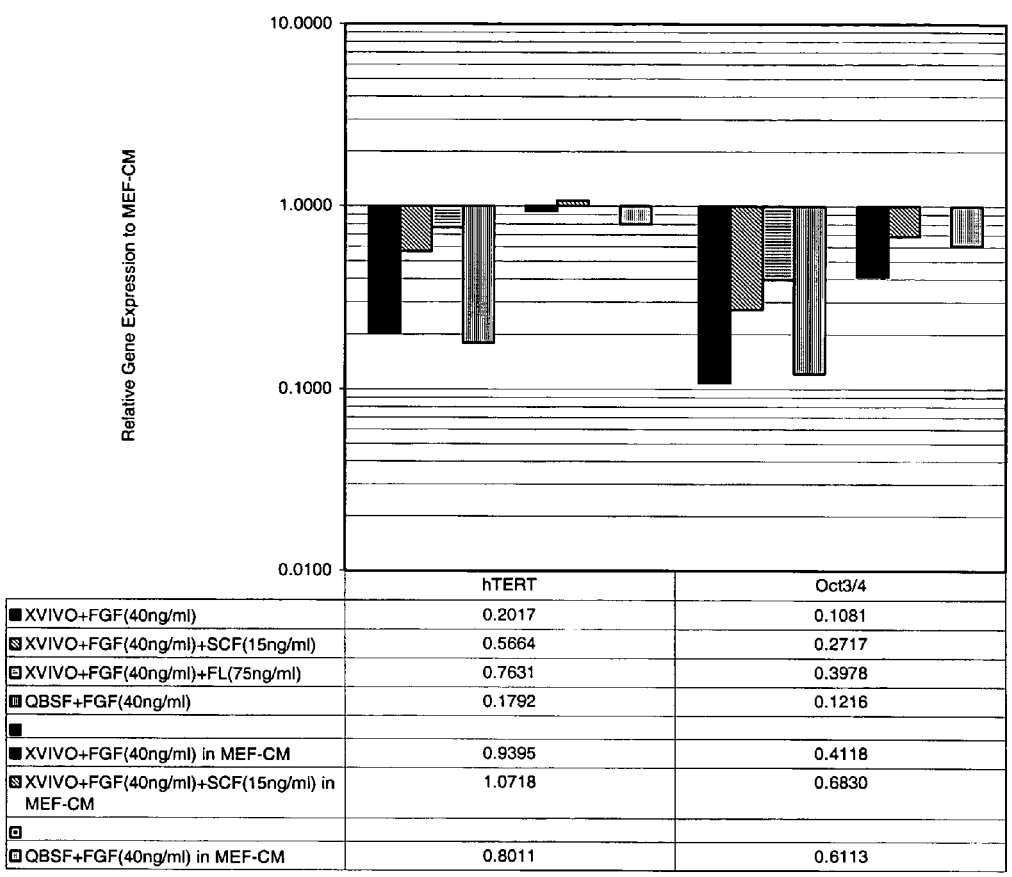

FIG. 7 shows the gene expression profile of hTERT and Oct 3/4, measured by real time RT-PCR, as described in Example 5.

Figure 8:
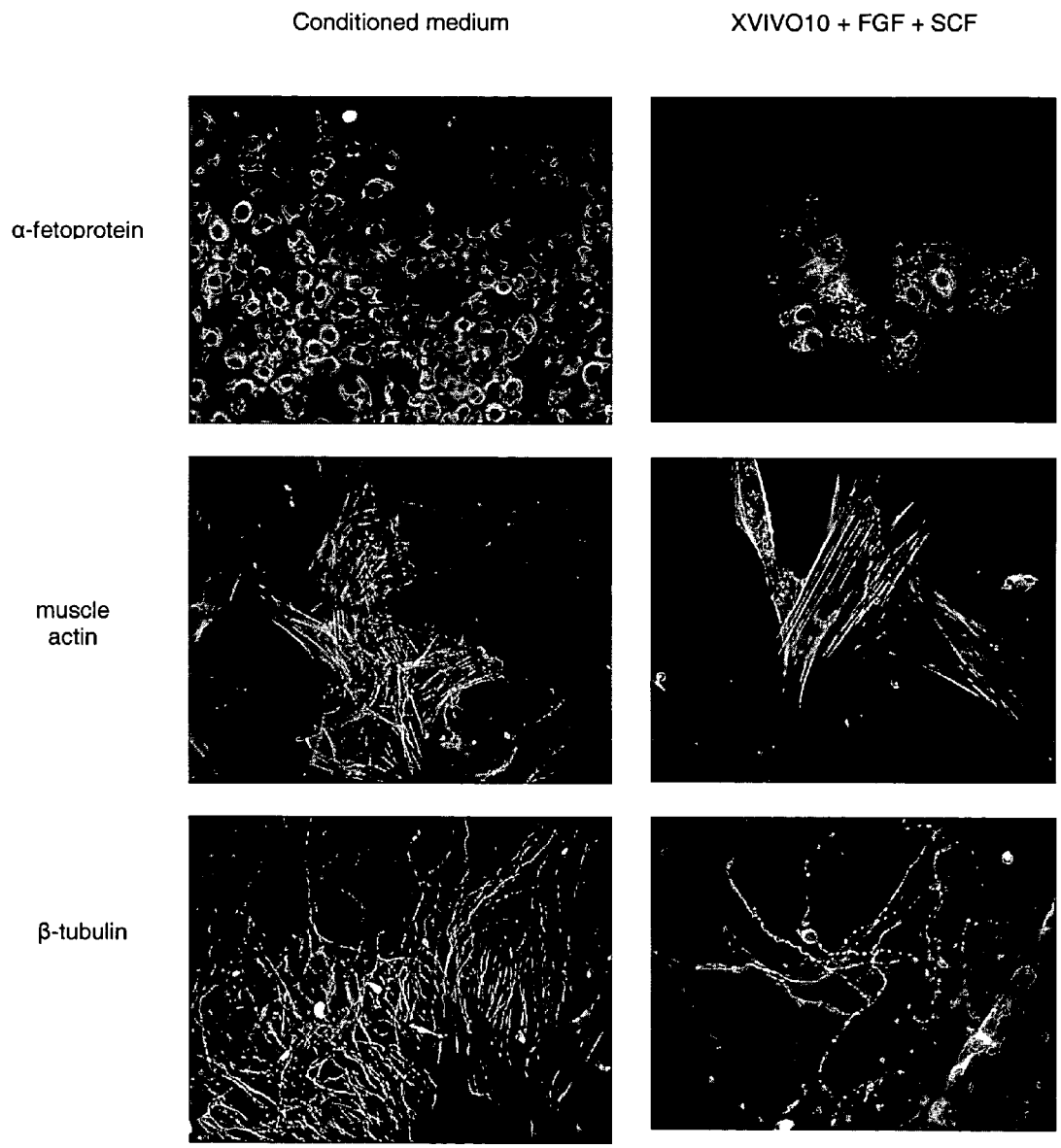

FIG. 8 demonstrates that cells cultured in unconditioned medium retain their pluripotency. hES cells passaged 7 times in mEF conditioned medium, or unconditioned X-VIVO™ 10 medium containing bFGF and SCF. The cells were then differentiated into embryoid bodies, plated, and analyzed by immunocytochemistry for phenotypic markers representing each of the three germ layers. The cells stain for α-fetoprotein (representing endoderm); muscle actin (representing mesoderm), and β-tubulin III (representing ectoderm). The cells grown in the culture system described in this patent application are suitable for making a wide scope of differentiated cell types.

Figure 9:
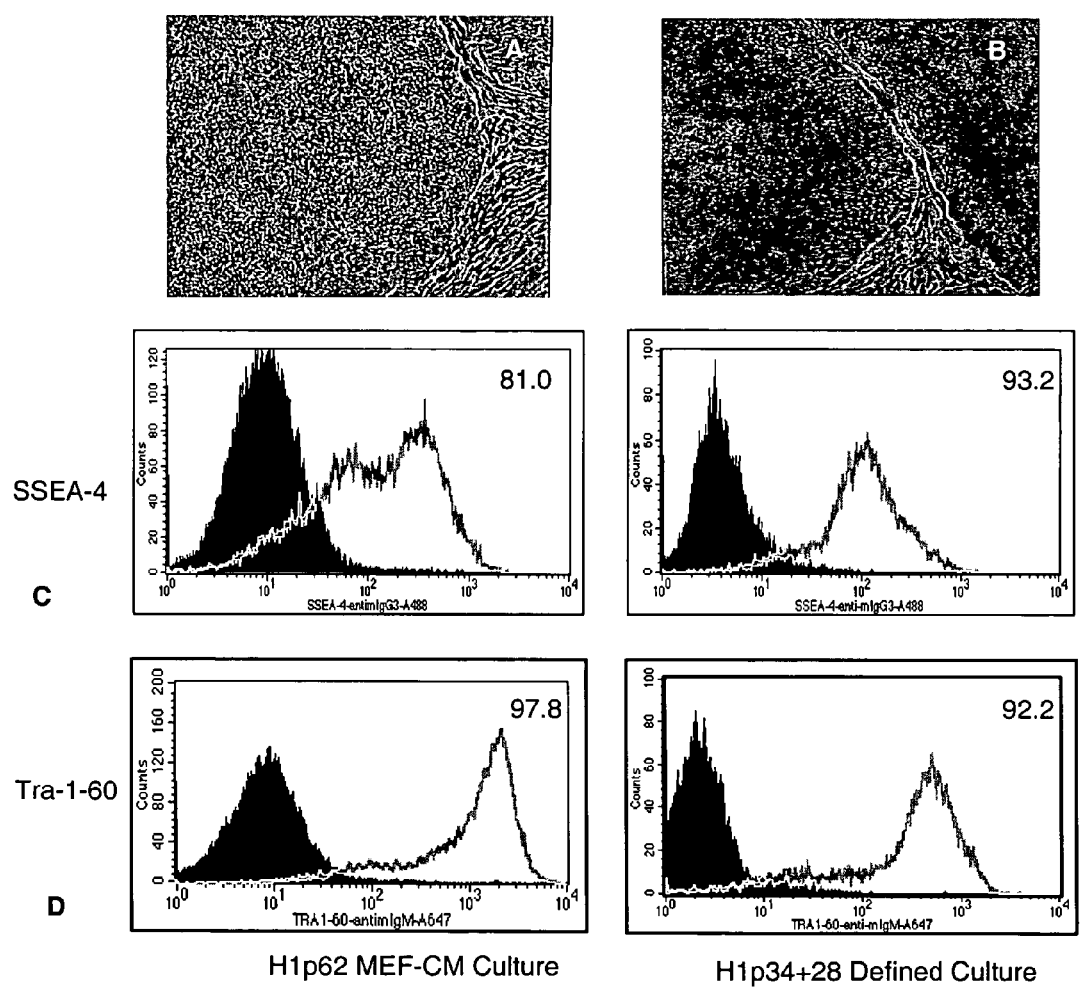

FIG. 9 shows the morphology of undifferentiated hES cell cultures growing in mEF conditioned medium on Matrigel® (Panel A), compared with cultures growing in defined medium containing 80 ng/mL FGF on laminin (Panel B). Also shown is a comparison of the hES cell markers SSEA-4 (Panel C) and Tra-1-60 (Panel D). Culture performance in the defined medium on laminin was superior: very large ES cell colonies were observed, representing ~80% of the culture.

Figure 10:
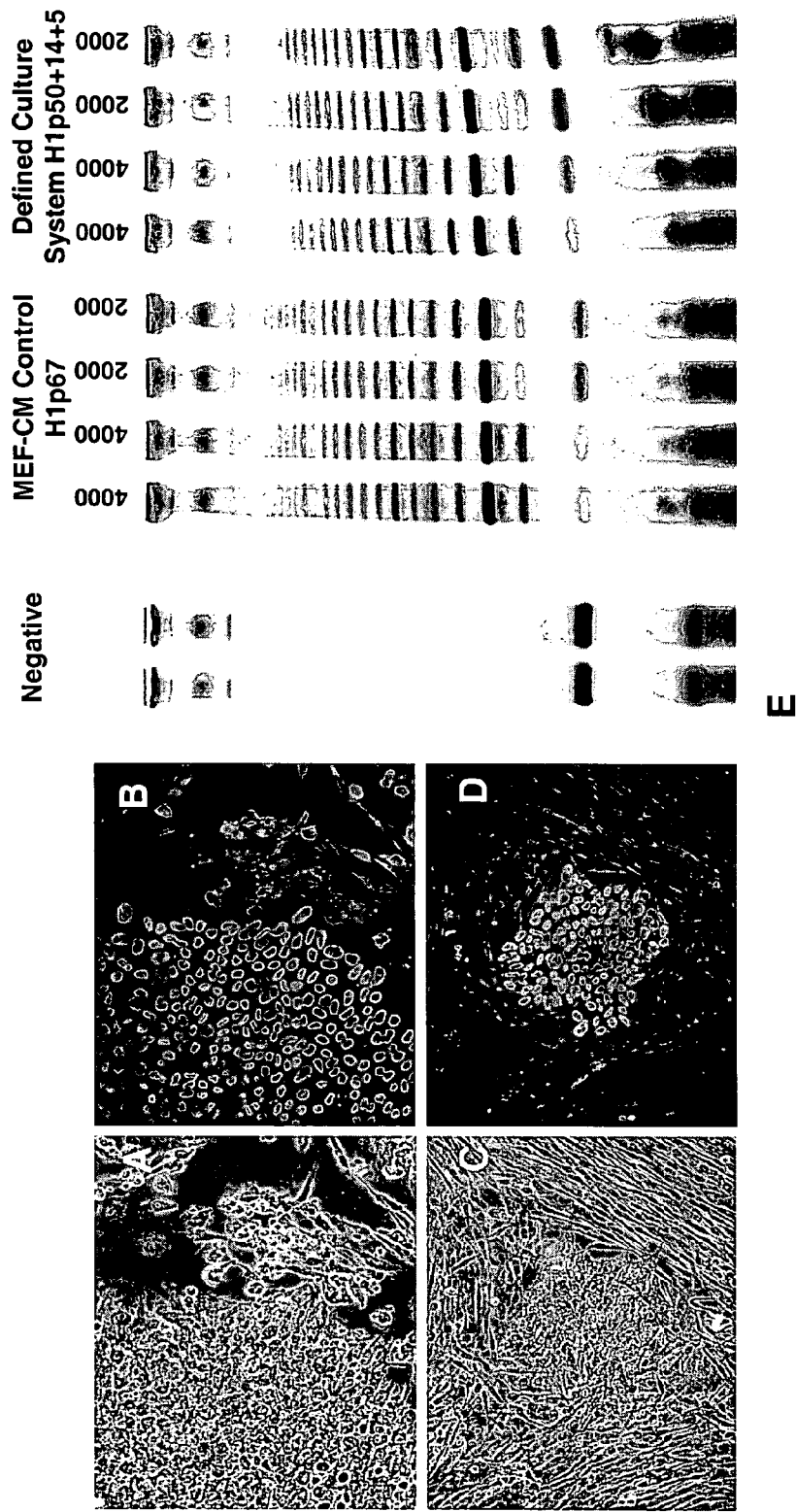

FIG. 10 shows cultures of hES cells growing in defined medium on laminin by phase contrast (Panels A and C) and by staining for Oct 3/4 expression (Panels B and D). Panel E shows TRAP analysis for telomerase activity. BY all these criteria, hES cells grown in medium containing 80 ng/mL have all the characteristics of undifferentiated pluripotent cells.

Figure 11:
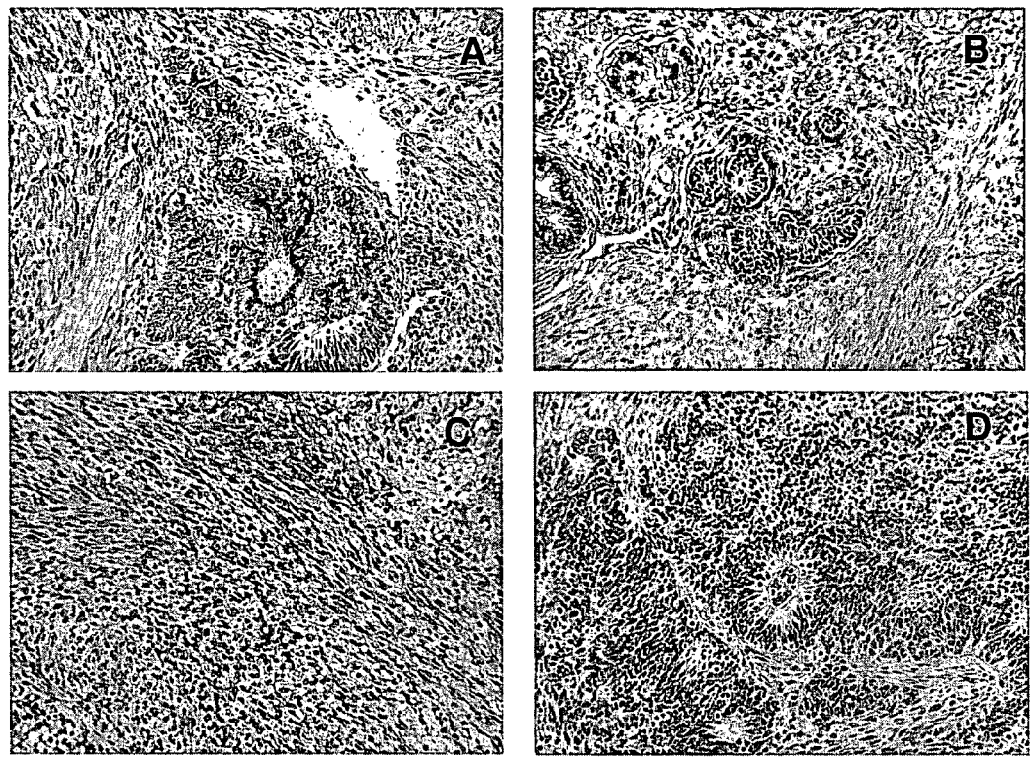

FIG. 11 shows teratomas derived from hES cells grown in these conditions (200X). Panel A: Pigmented epithelium (endoderm); Panel B: Renal tissue (endoderm); Panel C: Mesenchymal tissue (mesoderm); Panel D: Neural tubes (ectoderm)—representing all three germ layers.

DETAILED DESCRIPTION

Previous technology for growing primate pluripotent stem (pPS) cells has required that the cell culture environment contain cells or cell supernatants from other species to inhibit differentiation while they proliferate. This requirement complicates commercialization and therapeutic use of these cells, because the reagents are not easy to standardize, and constitute a potential source of contamination.

This disclosure provides an improved system for rapidly expanding pPS cells in vitro without requiring a layer of feeder cells to support the culture—either in direct contact with the pPS cells, or for preconditioning the medium in which the pPS cells are cultured.

As a result of thorough investigation of the features required, it has now been determined that the beneficial effect of the feeder cells can be replaced by providing a mixture of soluble factors. It turns out that the presence of feeder cell components is not required, as long as the signal transduction pathways required for undifferentiated growth are adequately activated by factors in the culture environment.

Figure 1:
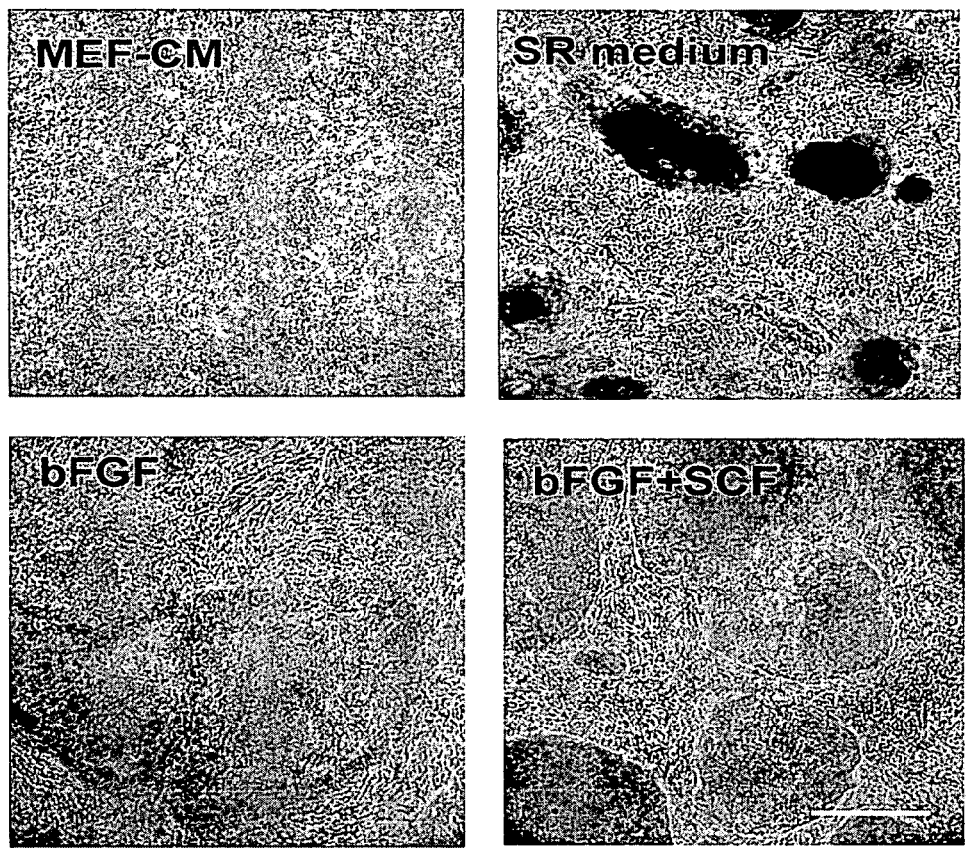
Figure 3:
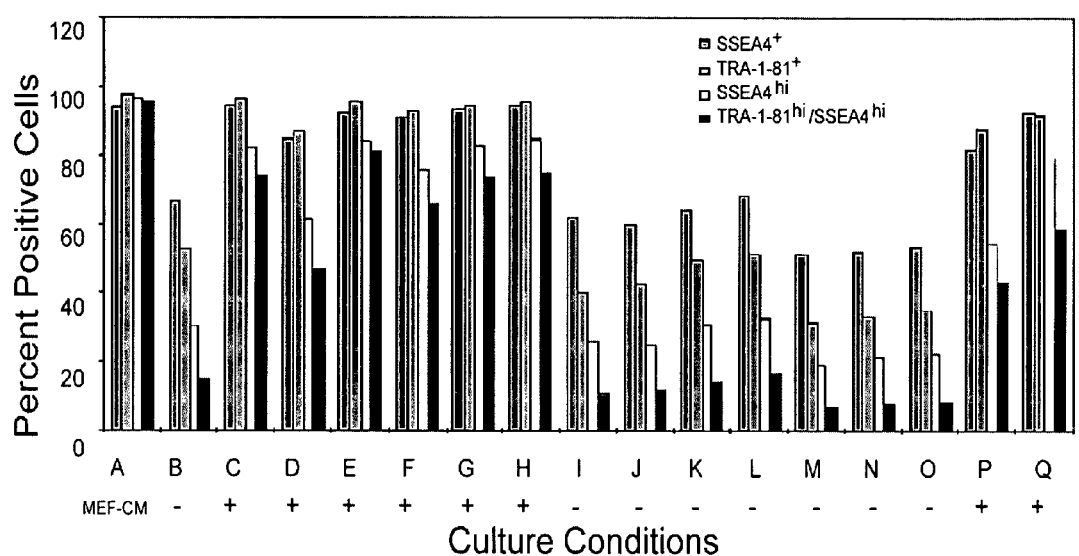

This disclosure shows inter alia how pPS cells can be grown in medium that has not been preconditioned, but has been supplemented with ingredients that perform essentially the same function as factors secreted from feeder cells. Certain factor combinations comprising moderate to high levels of fibroblast growth factors and other cells generate cultures that can proliferate 20-fold or more through 6 or more passages, while maintaining a majority of the cells in the culture in an undifferentiated state (FIGS. 1, 3, and 6). Near confluence, most of the cells have morphological features of undifferentiated cells, and express characteristic phenotypic markers: SSEA-4, Tra-1-60, Tra-1-81, Oct-4, Cripto, and telomerase reverse transcriptase (TERT). The cultures retain their pluripotency, demonstrated by their ability to form differentiated cells representing all three germ layers.

It has been discovered that an unusually high concentration of FGF in a suitable base nutrient medium is often adequate to maintain human embryonic stem (hES) cells in a substantially undifferentiated form. This is counter-intuitive, because FGF is thought to drive cells towards the formation of fibroblasts. There has been no previous suggestion to increase FGF concentrations in the culture medium for any cell type, once serum has been removed from the culture.

Quite surprisingly, it has now been found that hES cells grown in high FGF containing medium with glutamine and bicarbonate expand substantially more rapidly than hES cells grown on feeder cells or in conditioned medium, while maintaining their undifferentiated phenotype. The reasons for this are unclear; nor was it predictable based on what was previously known about hES cell culture. Nevertheless, this finding is important, because it provides a rapid expansion method for producing commercial grade undifferentiated hES cells on a commercial scale. Now that this technology is available, the production of pluripotent stem cells for treating human patients in need of tissue regeneration holds considerable promise.

The techniques provided in this invention represent an important advance in the potential use of pluripotent stem cells for research and therapeutic use. Further advantages of the invention will be understood from the sections that follow.

Definitions

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture.

Included in the definition of pPS cells are embryonic cells of various types, exemplified by human embryonic stem (hES) cells, defined below; embryonic stem cells from other primates, such as Rhesus or marmoset stem cells (Thomson et al., Proc. Natl. Acad. Sci. USA 92:7844, 1995; Developmental Biology 38:133, 1998); and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

Prototype "human Embryonic Stem cells" (hES cells) are described by Thomson et al. (Science 282:1145, 1998; U.S. Pat. No. 6,200,806). The scope of the term covers pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells on an ongoing basis, and may contain at least 40%, 60%, or 80% in order of increasing preference (in terms percentage of cells with the same genotype that are undifferentiated).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells that can be co-cultured with pPS cells to allow them to proliferate without differentiation. pPS cell populations are said to be "essentially free" of feeder cells if the cells have been grown through at least one round after splitting in which fresh feeder cells are not added to support the growth of pPS cells. A feeder free culture will contain less than about ~5% feeder cells. Compositions containing less than 1%, 0.2%, 0.05%, or 0.01% feeder cells (expressed as % of total cells in the culture) are increasingly more preferred.

A "growth environment" is an environment in which cells of interest will proliferate in vitro. Features of the environment include the medium in which the cells are cultured, and a supporting structure (such as a substrate on a solid surface) if present.

A "nutrient medium" is a medium for culturing cells containing nutrients that promote proliferation. The nutrient medium typically contains isotonic saline, buffer, a protein source (in the form of one or more added proteins or amino acids), and potentially other exogenously added nutrients and growth factors.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

A "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

A "commercial product" is any product or product combination that is manufactured for distribution from one entity to another entity for any purpose, with or without financial compensation or other consideration from the other entity. Exemplary is a culture medium or culture environment, with or without other reagents, containers, or apparatus for use in culturing cells, and with or without written information.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current Protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Other texts are *Creating a High Performance Culture* (Aroselli, Hu. Res. Dev. Pr. 1996) and *Limits to Growth* (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Sources of Pluripotent Stem Cells

Suitable source cells for culturing and differentiation according to this invention include established lines of pluripotent cells derived from tissue formed after gestation. Exemplary primary tissue sources are embryonic tissue (such as a blastocyst), or fetal tissue taken any time during gestation, typically but not necessarily before 10 weeks gestation. Non-limiting exemplars are established lines of primate embryonic stem (ES) cells, exemplified below; and embryonic germ (EG) cells, described in Shamblott et al., Proc. Natl. Acad. Sci. USA 95:13726, 1998; and U.S. Pat. No. 6,090,622. Also contemplated is use of the techniques of this disclosure during the initial establishment or stabilization of such cells, in which case the source cells would be primary pluripotent cells taken directly from the tissues listed.

Establishing Lines of Human Embryonic Stem (hES) Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

Materials for the preparation of hES cell lines according to traditional methods are as follows. Serum-containing ES medium is made with 80% DMEM (typically knockout DMEM), 20% defined fetal bovine serum (FBS), 1% non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement (Gibco #10828-028), 1% non-essential amino acids, 1 mM L-glutamine, and 0.1 mM β-mercaptoethanol. Just before use, human bFGF is added to a final concentration of 4-8 ng/mL.

Mouse embryonic fibroblasts (mEF) for use as feeder cells can be obtained from outbred CF1 mice (SASCO) or other suitable strains, as described in U.S. Pat. No. 6,200,806 (Thomson) and WO 01/51616 (Geron Corp.). Also suitable as feeder cells are telomerized cell lines, and human cell lines obtained from differentiating pPS cells (US-2002-0072117-A1) or other primitive cell types. Feeder cells can be propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 as needed to keep the cells subconfluent. To prepare the feeder cell layer, cells are irradiated at a dose to inhibit proliferation but permit synthesis of important factors that support hES cells (~4000 rads γ-irradiation). The layers are used 5 h to 4 days after plating. The medium is replaced with fresh hES medium just before seeding.

hES cells can be isolated from human blastocyst obtained from human in vivo preimplantation embryos, in vitro fertilized embryos, or one cell human embryos expanded to the blastocyst stage (Bongso et al., Hum Reprod 4: 706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase (Sigma). The inner cell masses are isolated by immunosurgery or by mechanical separation, and plated on mouse embryonic feeder layers, or in feeder free culture as described below.

After 9 to 15 days, inner cell mass-derived outgrowths are dissociated into clumps either by exposure to calcium and magnesium-free phosphate-buffered saline (PBS) with 1 mM EDTA, by exposure to dispase, collagenase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated.

ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette.

Propagation of pPS Cells in the Absence of Feeder Cells

This invention allows pPS to be propagated in an undifferentiated state, even in the absence of feeder cells. Feeder-free pPS cell cultures can be obtained either by passaging cells grown on feeder into feeder-free conditions, or by first deriving the cells from blastocysts into a feeder-free environment.

In the absence of feeders, the pPS cells are cultured in an environment that supports proliferation without differentiation. Aspects of culture that can affect differentiation include the substrate upon which the cells are cultured, the medium in which they are cultured, and the manner in which they are split and passaged to new culture environments.

pPS cells can be supported in feeder-free culture on an extracellular matrix. The matrix can be deposited by preculturing and lysing a matrix-forming cell line (WO 99/20741), such as the STO mouse fibroblast line (ATCC Accession No. CRL-1503), or human placental fibroblasts. The matrix can also be coated directly into the culture vessel with isolated matrix components. Matrigel® is a soluble preparation from Engelbreth-Holm-Swarm tumor cells that gels at room temperature to form a reconstituted basement membrane. Other suitable extracellular matrix components may include laminin, fibronectin, proteoglycan, vitronectin, entactin, heparan sulfate, and so on, alone or in various combinations. The matrix components may be human, and/or produced by recombinant expression. Substrates that can be tested using the experimental procedures described herein include not only other extracellular matrix components, but also polyamines, and other commercially available coatings. This invention contemplates adding extracellular matrix to the fluid phase of a culture at the time of passaging the cells or as part of a regular feeding. This invention also contemplates extracellular matrix deposited into the culture by cells within the culture (such as stromal cells that have formed from the pPS cell line around the periphery of an undifferentiated colony).

The pluripotent cells are plated onto the substrate in a suitable distribution and in the presence of a medium that promotes cell survival, propagation, and retention of the desirable characteristics. These characteristics benefit from careful attention to the seeding distribution. Plating densities of at least ~15,000 cells $cm^{-2}$ (typically 90,000 $cm^{-2}$ to 170,000 $cm^{-2}$) promote survival and limit differentiation. In one method, enzymatic digestion is halted before cells become completely dispersed (say, ~5 min with collagenase IV). The plate is then scraped gently with a pipette, and the cells are triturated into clumps of adherent cells, about 10-2000 cells in size, which are then passaged into the new culture environment.

Alternatively, primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with 0.05% (wt/vol) trypsin and 0.053 mM EDTA for 5-15 min at 37° C. The remaining cells in the plate are removed, triturated with the pipette until dispersed into single cells and small clusters, and then replated. In another illustration, the cells are harvested without enzymes before the plate reaches confluence. The cells are incubated ~5 min in 0.5 mM EDTA alone in PBS, washed from the culture vessel, and then replated without further dispersal.

pPS cells plated in the absence of fresh feeder cells benefit from being cultured in a nutrient medium. The medium will generally contain the usual components to enhance cell survival, including isotonic buffer (i.e., a buffer that is isotonic when adjusted to working concentration), essential minerals, and either serum or a serum replacement of some kind. To inhibit differentiation, the medium is formulated to supply some of the elements provided by feeder cells or their equivalents.

The base nutrient medium used can have any of several different formulae. Exemplary serum-containing ES medium is made with 80% DMEM (typically KO DMEM), 20% defined fetal bovine serum (FBS), 1% non-essential amino acids, 1 mM L-glutamine, and 0.1 mM β-mercaptoethanol. Serum-free ES medium is made with 80% KO DMEM, 20% serum replacement (SR: Gibco #10828-028), 1% non-essential amino acids, 1 mM L-glutamine, and 0.1 mM β-mercaptoethanol.

Medium Additives

The nutrient medium used for culturing the pPS cells comprises one or more factors that promote proliferation of the pPS cells without differentiation. As will be apparent from the following description, the supplementation can occur by pre-culturing the medium with cells that secrete such factors, by adding such factors to the medium artificially, or by both techniques in combination.

Conditioned medium can be prepared by culturing irradiated primary mouse embryonic fibroblasts or other feeder cells at a density of ~5-6×10$^4$ cm$^{-2}$ in a serum free medium such as KO DMEM supplemented with 20% serum replacement and ~4-8 ng/mL basic fibroblast growth factor (bFGF). The culture supernatant is harvested after ~1 day at 37° C. The cells are cultured in the medium for sufficient time to allow adequate concentration of released factors that support pPS cell culture. Typically, medium conditioned by culturing for 24 hours at 37° C. contains a concentration of factors that support pPS cell culture for at least 24 hours. However, the culturing period can be adjusted upwards or downwards, determining empirically what constitutes an adequate period. Medium that has been conditioned for 1-2 days is typically used to support pPS cell culture for 1-2 days, and then exchanged.

Non-conditioned medium that supports pPS cell growth in an undifferentiated state can be created by adding to a suitable base medium certain factors that invoke the appropriate signal transduction pathways in undifferentiated cells.

Suitable base media include ES cell medium with 20% serum replacement, as already described. Other base media that can be used for this purpose are commercially available for culturing proliferative cell types like hematopoietic cells. Exemplary are X-VIVO™ 10 expansion medium (Biowhittaker) and QBSF™-60 (Quality Biological Inc.) (Example 4). See also WO 98/30679 (Life Technologies Inc.) and U.S. Pat. No. 5,405,772 (Amgen). The medium will typically contain a neutral buffer (such as phosphate and/or high concentration bicarbonate) in isotonic solution; and protein nutrient, in the form of serum (such as FBS), serum replacement (SR), albumin (e.g., isolated or recombinant human albumin), or essential and non-essential amino acids (such as glutamine) in an effective combination. It will also typically contain lipids, fatty acids, or cholesterol as artificial additives or the HDL or LDL extract of serum. Other beneficial factors that can be included are growth-inducing hormones like insulin or transferrin, nucleosides or nucleotides, pyruvate, a sugar source (such as glucose), selenium (in any ionized form or salt), a glucocorticoid (such as hydrocortisone) or other substance that inhibits activation of inflammatory pathways, or a reducing agent (such as β-mercaptoethanol).

It has been discovered that adding a fibroblast growth factor at high concentration is especially effective to promote hES cell proliferation without differentiation. Exemplary are basic FGF (FGF-2), and FGF-4, but other members of the family can also be used. Equivalent forms as species homologs, artificial analogs, antibodies to the respective FGF receptor, and other receptor activating molecules. It has been determined from gene expression analysis that undifferentiated hES cells express receptors for acidic FGF (FGF-1). At a high concentration, FGF alone is sufficient to promote growth of hES cells in an undifferentiated state (Examples 5 and 6). Concentrations of FGF effective for promoting undifferentiated pPS cell growth on their own usually have a lower bound of about 20, 30, or 40 ng/mL, with a practical upper bound of about 200, 500, or 1000 ng/mL. Concentrations of at least 60, 80, or 100 ng/mL bFGF are both reliable and cost effective. Equivalent concentrations of other forms and analogs of FGF can be determined empirically by weaning cultures from bFGF into the proposed substitute, and monitoring the culture for differentiation according to the marker system described below.

As a supplement to FGF, ligands that bind c-kit, such as stem cell factor (SCF, Steel factor), antibodies to c-kit, and other activators of the same signal transduction pathway may also be beneficial. SCF is dimeric and occurs in soluble and membrane-bound forms. It transduces signals by ligand-mediated dimerization of c-kit, which is a receptor tyrosine kinase related to the receptors for platelet-derived growth factor (PDGF), macrophage colony-stimulating factor, Flt-3 ligand and vascular endothelial growth factor (VEGF). Addition of 15 ng/mL Flt-3 ligand or SCF to medium containing 40 ng/mL bFGF improves culture characteristics—in fact, 15 ng/mL Flt-3 ligand plus 40 ng/mL FGF is about as effective as 80 ng/mL bFGF alone (Examples 5 and 6). Other possible additives are factors that elevate cyclic AMP levels, such as forskolin; factors that induce gp 130, such as LIF or Oncostatin-M; and hematopoietic growth factors, such as thrombopoietin (TPO) (Example 3). Also of interest is transforming growth factor β1 (TGFβ1) (M. Amit et al., Biol. Reprod. 70:837, 2004). Such factors or their equivalents may be used individually or in an effective combination with other influential factors in the medium, as already described.

Whenever these media are built from scratch, it is possible to use extracts of human serum, human recombinant proteins, and biosynthetic components in any suitable combination, thereby avoiding the use of any component originating from non-human vertebrate animals. The media may be "defined", which means that undefined mixtures or extracts (e.g., protein or lipid blends obtained from serum or other sources) are avoided in favor of purified components of known composition. Each of these properties has advantages in terms of the reproducibility and reliability of the formulation, and satisfaction of regulatory issues relating to the use of pPS derived products in human clinical therapy.

Desirable Outcomes

A medium formulation can be tested for its ability to support pPS cells by swapping it into a feeder-free culture system in place of medium conditioned by primary mouse embryonic fibroblasts (mEF), or some other proven standard (Examples 3, 5, and 6). If pPS cells grow in a substantially undifferentiated state, then the medium can be characterized as supporting pPS cells in feeder free culture.

One of the virtues of using fresh medium in this culture system is the ability to adjust conditions so that the cells expand more rapidly than they do when cultured on feeder cells according to traditional techniques, or in conditioned medium. Populations of pluripotent stem cells can be obtained that are 10-, 20-, 50-, 100-, or 1000-fold expanded when compared to the starting population. Under suitable conditions, cells in the expanded population will be 50%, 70% or more in the undifferentiated state.

The degree of expansion per passage is calculated by dividing the number of cells harvested at the end of the culture by the number of cells originally seeded into the culture. Where geometry of the culture environment is limiting or for other reasons, the cells may optionally be passaged into a similar culture environment for further expansion. The total expansion is the product of all the expansions in each of the passages. Of course, it is not necessary to retain all the expanded cells on each passage. For example, if the cells expand 2-fold in each culture, but only ~50% of the cells are retained on each passage, then approximately the same number of cells will be carried forward. But after four cultures, the cells are said to have undergone an expansion of 16-fold.

Cultures of hES cells on mouse embryonic fibroblast (mEF) feeder cells, or in mEF conditioned medium, have a doubling time of about 31-33 hours (Example 1). Certain culture environments of this invention comprising fresh medium support doubling of hES cells in less than ~24 hours (Example 5), potentially in less than ~16 hours. In terms of expansion upon regular passaging in standard culture wells, the system can be used to expand hES cells by 10- to potentially 50-fold per week. Improved efficiency is believed to be the result both of the more rapid doubling time, and the higher proportion of pPS cells that take in the new environment after passaging.

Of course, culture conditions inappropriate for pPS cells will cause them to differentiate promptly. However, the reader should be aware that marginally beneficial conditions may allow pPS cells to go through a few passages while still retaining a proportion of undifferentiated cells. In order to test whether conditions are adequate for indefinite culture of pPS cells, it is recommended that the cells be expanded at least 10- or 20-fold though at least four passages. A higher degree of expansion and/or a higher number of passages (e.g., at least 7 passages and 50- or 100-fold expansion) provides a more rigorous test. It is permissible for a few phenotypic markers to undertake a quantitative adjustment befitting adaptation to particular conditions (say, up or down 2- or 5-fold)—they will typically revert to previous levels when the cells are placed back into their previous environment (Example 5).

An effective test for whether a cell is still pluripotent is the demonstration that it can still be caused to differentiate into progeny that represents (or bears antibody or PCR-detectable phenotypes) of each of the three embryonic germ layers. As a proxy, the user may identify the undifferentiated phenotype using the marker system described in the next section.

Nutrient medium and other culture characteristics formulated according to this invention can be adapted to any culture device suitable for growing pPS cells. Devices having a suitable surface include regular tissue culture wells, T-flasks, roller bottles, gas-permeable containers, and flat or parallel plate bioreactors or cell factories. Also contemplated are culture environments in which the pPS cells are attached to microcarriers or particles kept in suspension in stirred tank vessels. Fresh medium can be introduced into any of these environments by batch exchange (replacement of spent medium with fresh medium), fed-batch process (fresh medium added with no removal), or ongoing exchange in which a proportion of the medium is replaced with fresh medium on a continuous or periodic basis.

Characteristics of Undifferentiated pPS Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

When cells are split and passaged between cultures, some cells may differentiate (particularly when replated as single cells at low density, or when large clusters are allowed to form). However, cultures typically reestablish a larger proportion of undifferentiated cells as they reapproach confluence.

hES and hEG cells can also be characterized by expressed cell markers detectable by antibody (flow cytometry or immunocytochemistry) or by reverse transcriptase PCR. Human ES cells typically have antibody-detectable SSEA-4, Tra-1-60, and Tra-1-81, but little SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Cultures can also be characterized according to gene expression determined at the mRNA level. Panels of suitable markers are listed in application US 2003/0224411 A1 (Geron Corp.) Exemplary are Cripto, gastrin-releasing peptide (GRP) receptor, podocalyxin-like protein (PODXL), human telomerase reverse transcriptase (hTERT), and the POU transcription factor Oct 3/4. Telomerase enzyme activity (characteristic of pPS cells) can be measured by TRAP assay (Example 6). The cultures can also be back-screened against markers of differentiated cells, which should be low if the culture system is promoting proliferation without differentiation. Such markers may include CD44, CD105 (endoglin), CD106 (VCAM-1), CD90 (Thy-1), STRO-1, Vimentin, and Human Thymus Stroma.

Another desirable feature of propagated pPS cells is a potential to differentiate into cells of all three germ layers: endoderm, mesoderm, and ectoderm. Pluripotency of hES cells can be confirmed by forming teratomas in SCID mice, and examining them for representative tissues of all three germ layers. Alternatively, pluripotency can be determined by allowing pPS cells to differentiate non-specifically (for example, by forming embryoid bodies), and then determining the cell types represented in the culture by immunocytochemistry (FIG. 6). Potential of pPS cells to differentiate into particular cell lines can be determined according to procedures described in the next section.

Uses of Propagated pPS Cells

This description provides a method by which large numbers of pluripotent cells can be produced commercially without the need of feeder cells. The cells are useful for a number of research and commercial purposes in the undifferentiated form, or can be directed to differentiate into a particular cell type.

Screening Proliferation Factors, Differentiation Factors, and Pharmaceuticals

Undifferentiated pPS cells can be used to screen for factors (such as small molecule drugs, peptides, polynucleotides, and the like) or conditions (such as culture conditions or manipulation) that affect the characteristics of pPS cells in culture. This system has the advantage of not being complicated by a secondary effect caused by perturbation of the feeder cells by the test compound. In one application, growth-affecting substances are tested. The conditioned medium is withdrawn from the culture and a simpler medium (such as KO DMEM) is substituted. Different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cells according to the test protocol, and then determining whether the treated cell develops functional or phenotypic characteristics of a differentiated cell of a particular lineage.

Feeder-free pPS cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp 375-410 in *In vitro Methods in Pharmaceutical Research*, Academic Press, 1997). Cytotoxicity can be determined by the effect on cell viability, survival, morphology, on the expression or release of certain markers, receptors or enzymes, on DNA synthesis or repair, measured by [$^3$H]-thymidine or BrdU incorporation, or on sister chromatid exchange, determined by metaphase spread. The reader is referred generally to the standard textbook *In vitro Methods in Pharmaceutical Research*, Academic Press, 1997, and U.S. Pat. No. 5,030, 015.

Differentiation of Propagated pPS Cells pPS cells cultured according to this invention can be used to make differentiated cells of various commercially and therapeutically important tissue types.

Clinically useful cell types can also be obtained from pPS cells, according to established differentiation protocols.

By way of illustration, neural cells can be generated from pPS cells according to the method described in International Patent Publication WO 01/88104 and application PCT/US02/19477 (Geron Corporation). Undifferentiated pPS cells or embryoid body cells are cultured in a medium containing one or more neurotrophins and one or more mitogens, generating a cell population in which at least ~60% of the cells express A2B5, polysialylated NCAM, or Nestin and which is capable of at least 20 doublings in culture. Exemplary mitogens are EGF, basic FGF, PDGF, and IGF-1. Exemplary neurotrophins are NT-3 and BDNF. The proliferating cells can then be caused to undergo terminal differentiation by culturing with neurotrophins in the absence of mitogen. Cell populations can be generated that contain a high proportion of cells staining for tyrosine hydroxylase, a characteristic of dopaminergic neurons.

Oligodendrocytes can be generated from pPS cells by culturing them as cell aggregates, suspended in a medium containing a mitogen such as FGF, and oligodendrocyte differentiation factors such as triiodothyronine, selenium, and retinoic acid. The cells are then plated onto a solid surface, the retinoic acid is withdrawn, and the population is expanded. Terminal differentiation can be effected by plating on poly-L-lysine, and removing all growth factors. Populations can be obtained in which over 80% of the cells are positive for oligodendrocyte markers NG2 proteoglycan, A2B5, and PDGFRα, and negative for the neuronal marker NeuN.

Hepatocytes can be generated from pPS cells according to the method described in U.S. Pat. No. 6,458,589 and PCT publication WO 01/81549 (Geron Corporation). Undifferentiated pPS cells are cultured in the presence of an inhibitor of histone deacetylase. In an exemplary method, differentiation is initiated with 1% DMSO (4 days), then 2.5 mM of the histone deacetylase inhibitor n-butyrate. The cells obtained can be matured by culturing 4 days in a hepatocyte culture medium containing n-butyrate, DMSO, plus growth factors such as EGF, hepatocyte growth factor, and TGF-α. Other effective hepatocyte differentiation protocols are described in U.S. Ser. No. 10/810,311.

Cardiomyocytes or cardiomyocyte precursors can be generated from pPS cells according to the method provided in WO 03/006950. The cells are cultured in a growth environment comprising fetal calf serum or serum replacement, and optionally a cardiotrophic factor that affects DNA-methylation, such as 5-azacytidine. Spontaneously contracting cells can then be separated from other cells in the population, by density centrifugation. Further process steps can include culturing the cells so as to form cardiac bodies, removing single cells, and then dispersing and reforming the cardiac bodies in successive iterations.

Hematopoietic cells can be made by coculturing pPS cells with murine bone marrow cells or yolk sac endothelial cells was used to generate cells with hematopoietic markers (U.S. Pat. No. 6,280,718). Hematopoietic cells can also be made by culturing pPS cells with hematogenic cytokines and a bone morphogenic protein, as described in US 2003/0153082 A1 and WO 03/050251.

Osteoblasts and their progenitors can be generated from pPS cells according to the method described in WO 03/004605. pPS-derived mesenchymal cells are differentiated in a medium containing an osteogenic factor, such as bone morphogenic protein (particularly BMP-4), a ligand for a human TGF-β receptor, or a ligand for a human vitamin D receptor. Cells that secrete insulin or other pancreatic hormones can be generated by culturing pPS cells or their derivatives in factors such as activin A, nicotinamide, and other factors listed in WO 03/050249. Chondrocytes or their progenitors can be generated by culturing pPS cells in microaggregates with effective combinations of differentiation factors listed in WO 03/050250.

pPS derived cells can be used for drug screening, preparing pharmaceutical compositions, research, and many other worthwhile purposes.

Commercial Distribution

Components of the culture system of this invention may be offered for sale, sold, or otherwise distributed from the place of manufacture for use by another entity for any purpose.

In one embodiment, a tissue culture media described in this application is distributed for use in maintaining or expanding pPS cells (exemplified by hES cells) in a substantially undifferentiated form, with or without subsequent differentiation into a particular mature cell type. The media can be constituted in any workable formulation, such as:

media ready for culture;
concentrated media to be diluted prior to use in culture;
powdered media (or any equivalent solid form) to be dissolved in water or an aqueous solvent prior to use in culture;
various components of the media (in solution, and/or in solid form) to be combined before use in culture.

Of course, such formulation options may be used in combination. For example, a media kit may comprise a base medium to be diluted to isotonic strength, plus concentrated and/or solid nutrients and growth factors to be combined into the medium to make up the desired medium constitution. Any reagent or set of reagents for commercial sale that makes up the media of this invention when properly assembled should be regarded as equivalent to the media per se, unless indicated otherwise.

In another embodiment, an extracellular matrix preparation or one or more isolated matrix components are distributed for use in maintaining or expanding pPS cells, according to this invention. Optionally, the extracellular matrix can be distributed in combination with the media: either in the same packaging, or as complementary components catalogued as being useful in a combined culture system. Optionally, the combination can also include a tissue culture device, or other equipment or reagents useful for culturing or characterizing the cells.

The products and product combinations are packaged in suitable containers, optionally in kit form, and may be accompanied by written information on the use of the materials according to this invention—such as maintaining or expanding pPS cells. The information may be written in any language on any communication medium accessible and understandable by the intended user. It may take the form of a label on the container or the kit, or a product insert packaged with the container and distributed together. Equivalent forms are descriptions, instructions, or explanations written in hard copy or in electronic form available to the user or the intended user as reference or resource material associated with the commercially distributed product.

The Examples that Follow are Illustrations Not Meant to Limit the Claimed Invention

EXAMPLES

Example 1

Growing hES Cells Without Feeder Cells in Conditioned Medium

In this example, undifferentiated hES cells that had been maintained on primary mouse embryonic feeder cells were maintained in the absence of feeders. The culture wells were coated with Matrigel®, and the cells were cultured in the presence of conditioned nutrient medium obtained from a culture of irradiated primary fibroblasts.

Conditioned medium (CM) was prepared as follows. The fibroblasts were harvested from T150 flasks by washing once with $Ca^{++}/Mg^{++}$ free PBS and incubating in trypsin/EDTA (Gibco). After the fibroblasts detached from the flask, they were collected in mEF medium (DMEM+10% FBS). The cells were irradiated at 4000 rad, counted and seeded at about 55,000 cells $cm^{-2}$ in mEF medium. After at least 4 hours, the medium was exchanged with SR containing ES medium. Conditioned medium was collected daily for feeding of hES cultures. Alternatively, medium was prepared using mEF plated in culture flasks, exchanging medium daily at 0.3-0.4 mL $cm^{-2}$. Before addition to the hES cultures, the conditioned medium was supplemented with 4 ng/mL of human bFGF (Gibco). Fibroblast cultures were used in this system for about 1 week, before replacing with newly prepared cells.

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 µL pipet tip under a microscope or by scraping and dissociating into small clusters. These cells were then seeded onto Matrigel® coated plates in conditioned medium (CM).

The day after seeding on Matrigel®, hES cells were visible as small colonies and there were cells in between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split using Collagenase IV, gently triturated into small clusters of 10-2,000 cells, and then re-seeded on Matrige® coated plates in conditioned medium at ~90,000 to 170,000 cells cm$^{-2}$. Medium was changed daily, and the cells were split and passaged again at 13 and 19 days after initial seeding.

Cultures of hES cells have been grown in the absence of feeder cells for over one year, with no apparent change in the proliferative capacity or phenotype. Human ES cells maintained on Matrigel® in mEF conditioned medium have a doubling time of about 31-33 hours, similar to the proliferation rate for hES cells grown on mEF feeder cells. H1 cells after 64 days of feeder-free culture showed a normal karyotype.

hES cells seeded onto laminin, fibronectin or collagen IV had colonies of undifferentiated hES cells, although the cultures on fibronectin or collagen IV did not contain as many undifferentiated colonies as the cultures on Matrigel® or laminin. When cells on Matrigel® or laminin reached confluence, the cells within the colonies became very compact, were morphologically very similar to the cells maintained on feeders and were serially passaged. After 40 days (6 passages), cells on Matrigel® and laminin contained a high proportion of colonies which continued to display ES-like morphology in long-term culture. However, cells maintained on fibronectin or collagen IV had fewer colonies displaying appropriate ES-morphology. As controls, cells cultured on Matrigel® or laminin in non-conditioned medium appeared to be proliferating more slowly and showed a differentiated morphology after a few passages.

Human ES cells maintained on Matrigel® in mEF conditioned medium showed a doubling time of about 31-33 hours, similar to the proliferation rate for hES cells grown on mEF feeder cells. Long-term culture in feeder free conditions can maintain a normal karyotype (Rosier et al., Dev Dyn. 229: 259, 2004; Carpenter et al., Dev Dyn. 229:243, 2004).

Example 2

Characterization of hES Cells Grown in Conditioned Medium

Undifferentiated hES cells express SSEA-4, Tra-1-60, Tra-1-81, OCT-4, and hTERT. In order to assess whether the cells maintained in feeder-free conditions retained these markers, cells were evaluated by immunostaining, reverse transcriptase PCR amplification, and assay for telomerase activity.

For analysis by fluorescence-activated cell sorting (FACS), the hES cells were dissociated in 0.5 mM EDTA in PBS and resuspended to about $5 \times 10^5$ cells in 50 µL diluent containing 0.1% BSA in PBS. They were labeled with specific primary antibody and then fluorescent second antibody, and analyzed on a Flow Cytometer.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells. SSEA-4, Tra-1-60, Tra-1-81, and alkaline phosphatase were expressed by the hES colonies on Matrigel® or laminin, as seen for the cells on feeders—but not by the differentiated cells in between the colonies.

Telomerase activity was measured by telomeric repeat amplification protocol (TRAP assay: Kim et al., Science 266: 2011, 1997; Weinrich et al., Nature Genetics 17:498, 1997). All the cultures conditions showed positive telomerase activity after 40 days on Matrigel®, laminin, fibronectin or collagen IV in mEF conditioned medium.

hES cells were also tested for their ability to form teratomas by intramuscular injection into SCID mice. Cells maintained on feeders or off feeders were harvested, resuspended in PBS and injected intramuscularly into SCID/beige mice ($5 \times 10^6$ cells per site). Tumors were excised and processed for histological analysis. Cystic epithelial structures, probable dental component, cartilage and glandular epithelial or neural components were found in teratomas derived from feeder-free hES cultures.

Example 3

Additives that Promote Undifferentiated ES Cell Growth in Fresh Medium

Experiments were conducted to investigate how different growth factors influence the proliferation and maintenance of undifferentiated hES cells of the H9 cell line.

hES medium contained 20% Serum Replacement (Gibco #10828-028), 80% Knockout DMEM (Gibco #10829-018), 1% non-essential amino acids (Gibco #11140-050), 1 mM L-glutamine (Gibco #15039-027), and 2.5 mM β-mercaptoethanol (Sigma #M7522). This medium was supplemented with 40 ng/mL bFGF; 15 ng/mL stem cell factor (SCF, R&D System #255SC); 100 ng/mL leukemia inhibitory factor (LIF, Sigma #L5283 or Chemicon #LIF 1010); 50 ng/mL ciliary neurotrophic factor (CNTF, R&D system #257-NT); 50 ng/mL recombinant human Oncostatin M (OSM, Sigma #O9635); and 15 ng/mL interleukin 6 (IL-6, R&D System #206-IL).

The H9 cell line (passage 31) was harvested from a culture in conditioned medium, plated onto Matrigel®, and cultured with hES medium with the factors at the concentrations indicated above, or 5- or 25-fold lower. Cells grown in the fully supplemented medium displayed undifferentiated hES morphology. A higher degree of differentiation was observed after four passages for the cultures grown at lower concentrations of the growth factors, and the cells maintained without growth factors were almost completely differentiated. These cultures were terminated.

After six passages, cells from the full-strength cocktail were replated onto Matrigel® as before, or onto laminin, which is free of the growth factors contained in the Matrigel® matrix. After eight passages, a large percentage of cells (~50-70%) in cultures grown on Matrigel® or laminin in this medium continued to display undifferentiated hES morphology. Some cells on Matrigel® or laminin were then passaged into hES medium containing added 40 ng/mL bFGF; but not SCF, LIF, CNTF, OSM, or IL-6. The cells continued to show an undifferentiated phenotype for the next four passages.

As detected by immunocytochemistry, expression patterns and levels of surface markers, including SSEA-1, SSEA-4, Tra 1-60 and Tra 1-81 in cultures maintained in high concentrations of growth factors were similar to cells maintained in MEF conditioned medium (MEF-CM). Cell lines stained positively for histocompatibility Class I antigen (HLA-ABC), and were negative in the isotype control (mslgG1). 50-70% of cells in cultures maintained in growth factors or MEF-CM expressed c-kit (a receptor for stem cell factor) while less than 20% of cells expressed gp130 (associated with the LIF receptor). This pattern supports the hypothesis that ligands for c-kit help support undifferentiated hES cell growth.

After 14 passages in the full-strength growth factor cocktail (~70 population doublings), about 50-70% of cells cultured on Matrigel® or laminin displayed morphology of undifferentiated hES cells, and had a normal karyotype. Cells cultured without any growth factor showed almost complete differentiation after 4 weeks in culture. A high degree of differentiation was also observed for cultures in which the growth factors had been diluted by 5- or 25-fold.

Additional experiments were done to dissect the components in the factor cocktail essential for hES cell growth. Cells of the H7 line were cultured in fresh hES medium containing the factor combinations shown in Table 2.

TABLE 2

Factors added to fresh ES medium for hES cell culture

| Condition | bFGF | Other Growth Factors |
|---|---|---|
| A | 8 mg/mL | |
| B | | |
| C | 40 ng/mL | |
| D | 40 ng/mL | SCF (15 ng/mL) |
| E | 40 ng/mL | Flt-3L (75 ng/mL) |
| F | 40 ng/mL | TPO (100 ng/mL) |
| G | 40 ng/mL | LIF (100 ng/mL) |
| H | 40 ng/mL | SCF (15 ng/mL), IL-6 (15 ng/mL), LIF (100 ng/mL), CNTF (50 ng/mL), OSM (50 ng/mL) |
| I | | SCF (15 ng/mL) |
| J | | SCF (100 ng/mL) |
| K | | Flt-3L (75 ng/mL) |
| L | | TPO (100 ng/mL) |
| M | | SCF (15 ng/mL), Flt-3L (75 ng/mL) |
| N | | SCF (15 ng/mL), TPO (100 ng/mL) |
| O | | SCF (100 ng/mL), Flt-3L (100 ng/mL), IL-6 (15 ng/mL) |
| P | 40 ng/mL | SCF (15 ng/mL), Flt-3L (75 ng/mL) |
| Q | 40 ng/mL | SCF (15 ng/mL), TPO (100 ng/mL) |

Cultures were passaged in these conditions and evaluated on an ongoing basis by morphological criteria. Many of the conditions continued to maintain considerable numbers of undifferentiated colonies.

FIG. 1 shows morphology of hES cells maintained for 6 passages in conditioned medium (mEF-CM), fresh SR medium alone, or fresh medium supplemented with 40 ng/mL bFGF or bFGF with stem cell factor. bar=800 μm.

Figure 2:
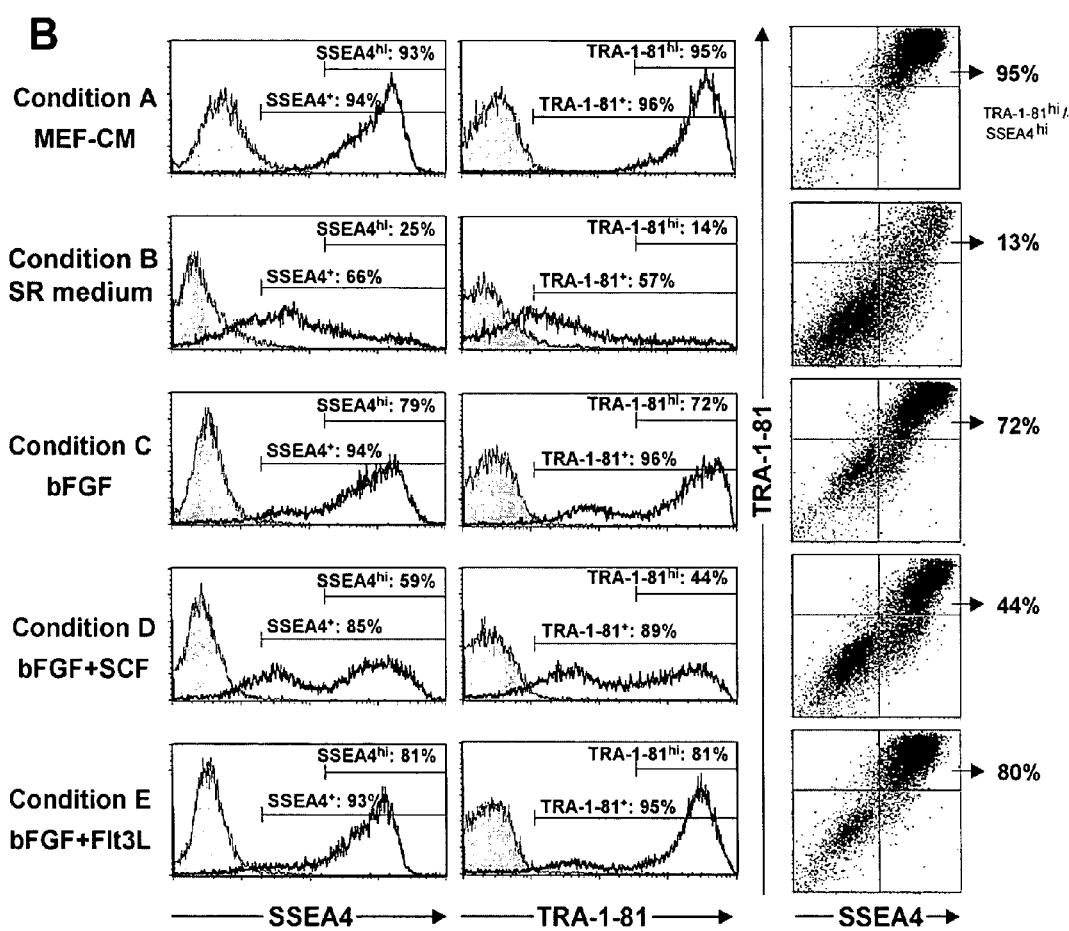

FIG. 2 shows immunocytometric analysis for expression of SSEA-4 and Tra-1-81. Conditions A, C, D, and E all maintained SSEA-4 and Tra-1-81 expression in a large proportion of the H7 cells. A subpopulation expressing these markers at high levels is also shown. Percentage of cells that show high-level staining for both TRA-1-81 and SSEA4 is indicated on the right side.

FIG. 3 compares SSEA-4 and Tra-1-81 staining amongst different growth conditions afar 6 passages. The presence of 40 ng/mL FGF (marked by "+") showed an undifferentiated phenotype comparable to cells grown in mEF conditioned medium; whereas combinations of growth factors without FGF (marked by "−") showed partial differentiation. These findings were confirmed using the H9 cell line. Undifferentiated colonies of H9 cells maintained in fresh medium containing bFGF at 40 ng/mL for 15 passages expressed SSEA-4, Tra-1-61, Tra-1-81 and alkaline phosphatase.

OCT3/4, hTERT, and cripto are markers for identifying the undifferentiated hES cell phenotype at the mRNA level (US-2003-0224411-A1). Quantitative real-time PCR assays were conducted to determine the expression of these markers in H7 cells after 6 passages. Cells cultured in bFGF-containing medium maintained expression of the markers at levels comparable to cells in mEF conditioned medium.

Figure 4:
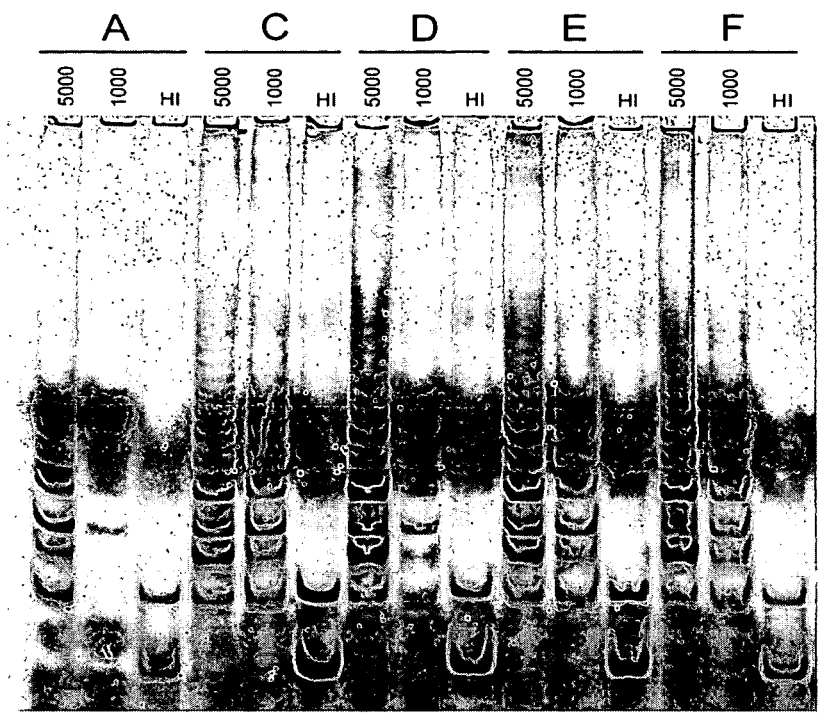
FIG. 4 shows that cells grown in high bFGF concentration are positive for telomerase activity (Panel A), and have a normal karyotype (the H7 cell line is female).
Figure 4:
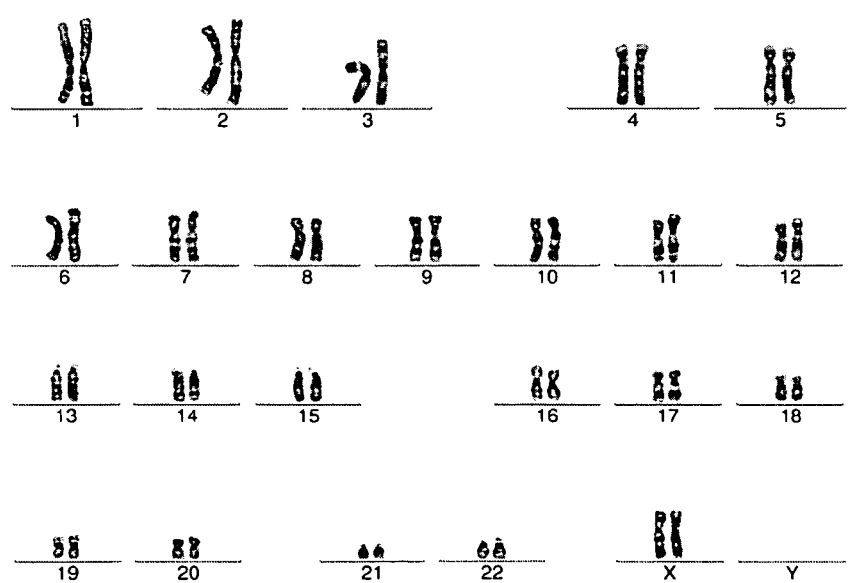

FIG. 4 shows telomerase activity and karyotype analysis of cells maintained in the factors listed in Table 2. Consistent with the expression of hTERT, hES cells maintained in bFGF alone or with other factors for 15 passages had telomerase activity as measured by TRAP assay. Cytogenetic analysis was performed using H7 cells maintained in MEF-CM, bFGF alone or with other factors (condition A, C, D, E, F, P and Q) for 15 passages. Cultures maintained a normal karyotype in all conditions except cultures in condition Q, where 4 of 30 metaphases were abnormal (trisomy 12). Three independent H9 cultures maintained in bFGF alone at passage 4 and 15 and one H9 cell culture maintained in bFGF+SCF+IL-6 (condition H) at passage 14 was also found to have a normal karyotype.

Figure 5:
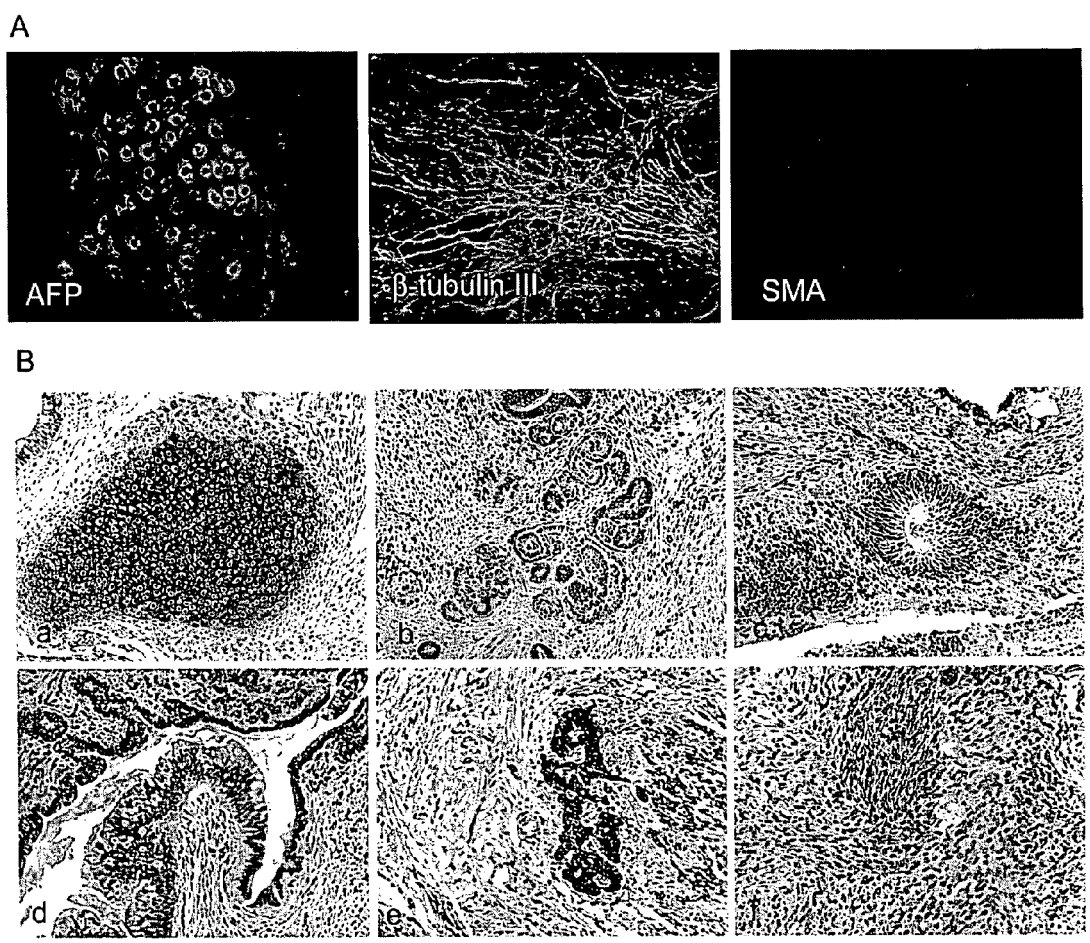
FIG. 5 shows that H7 hES cells maintained in high levels of bFGF that formed differentiated cells in tissue culture (Panel A), or generated teratomas when injected to SCID/beige mice (Panel B). Cells grown in fresh medium clearly retained their ability to differentiate into cells representing all three germ layers.

FIG. 5 shows that H7 hES cells maintained in bFGF alone or in combination with other factors through 15 passage retained their pluripotency. They readily formed embryoid bodies that were further differentiated for 7 days. Immunocytochemical analysis demonstrated cells staining positively for β-tubulin III, α-fetoprotein (AFP), or smooth muscle actin (Panel A). The hES cells also retained the capacity to generate teratomas when injected to SCID/beige mice (Panel B), like the cells grown in mEF conditioned medium. Histological analysis indicated the presence of multiple tissue structures including cartilage, primitive renal tissue, glandular epithelium, pigmented epithelium, nervous tissue and mesenchymal tissue. Therefore, cells grown in fresh medium containing high bFGF concentration retained their ability to differentiate into cells representing all three germ layers.

Example 4

Media for Growing hES Cells with Added FGF hES cells passaged 29 times in conditioned medium were weaned onto an alternative medium designed for proliferation and development of hematopoietic cells.

Ex vivo expansion medium was obtained by arrangement with a commercial supplier, and is thought to be based on the medium described in U.S. Pat. No. 5,405,772 (Ponting, Amgen Inc.). The Ponting medium comprises the following components: Iscove's modified Dulbecco's medium; amino acids; vitamins, bovine albumin; bovine transferrin (100 μg/mL); lipids and cholesterol; α-mercaptoethanol; pyruvate; nucleotides; epidermal growth factor (15 ng/mL); fibroblast growth factor (2 ng/mL); platelet-derived growth factor (10 ng/mL); and insulin (10 μg/mL). For use in the current experiments, the medium was further supplemented with 2 mM L-glutamine, 1% non-essential amino acids (Gibco), 0.1 mM β-mercaptoethanol, and 8 ng/mL bFGF.

The cells were first passaged onto Matrigel® coated plates using collagenase IV, and cultured for 2 days with conditioned medium. On day 2, the 100% conditioned medium was replaced with medium containing 80% conditioned medium plus 20% fresh expansion medium. Cells were fed fresh daily and passaged weekly. The proportion of expansion medium was increased by 20% approximately every 2 days until the cells were completely weaned, and then grown until they had been passaged a further 8 times.

At passages 1-4 in the expansion medium, the proportion of cells with the morphology of undifferentiated phenotype appeared to diminish slightly, but was restored by passage 8. When these cells were passaged back to medium conditioned by primary mouse embryonic fibroblasts, the cells were indistinguishable from those grown throughout the period in conditioned medium by the second passage.

To confirm that these cells retained their pluripotency, embryoid bodies were formed and analyzed by immunocytochemistry for phenotypic markers representing each of the three germ layers. After passage 4 in expansion medium, the cells were dissociated into small clumps using 200 U/mL collagenase IV at 37° C. for 10 min placed in suspension culture in differentiation medium (DMEM+10% or 20% FBS) for 4 days, then transferred onto poly-L-ornithine hydrobromide coated plates and cultured a further 10 days. They were fixed in 4% paraformaldehyde, permeabilized, and labeled alternately with mouse anti human β-tubulin isotype III clone SDL.3D10, mouse anti human muscle actin clone HHF35, or mouse anti α-fetoprotein. Primary antibody was visualized using FITC labeled goat anti-mouse IgG. Results showed that hES cells passaged repeatedly in expansion medium (not previously conditioned), and then differentiated, were positive for β-tubulin and muscle actin.

Example 5

Rapid Expansion Method for Producing Pluripotent Stem Cells hES cells passaged 20 times in conditioned medium were weaned onto an alternative medium designed for proliferation of human hematopoietic cells. X-VIVO™ 10 expansion medium was obtained from Biowhittaker; QBSF™-60 was obtained from Quality Biological Inc. The X-VIVO™ 10 formulation contains pharmaceutical grade human albumin, recombinant human insulin and pasteurized human transferrin. Exogenous growth factors, artificial stimulators of cellular proliferation or undefined supplements are not included in the X-VIVO™ 10 medium. They are also devoid of any protein-kinase C stimulators. QBSF™-60 is a serum-free formulation that contains recombinant or pasteurized human proteins. For use in these experiments, the X-VIVO™ 10 medium was supplemented with 2 mM L-glutamine, 1% non-essential amino acids (Gibco), 0.1 mM α-mercaptoethanol, and 8 ng/mL bFGF. The medium was further supplemented with 8 ng/mL or 40 ng/mL of bFGF (Gibco); 40 ng/mL of bFGF and 15 ng/mL of SCF (R & D System); or 40 ng/mL of bFGF and 75 ng/mL of Flt3 ligand (R & D System). QBSF™-60 medium was supplemented with 0.1 mM β-mercaptoethanol, 1% non-essential amino acids (Gibco) and 40 ng/mL of bFGF. hES cells cultured in mEF conditioned medium were used as control in these experiments.

The hES cells were first passaged onto Matrigel® coated plates using collagenase IV, and cultured for 2 days with conditioned medium. On day 2, the conditioned medium was replaced with 80% unconditioned ES medium plus 20% expansion medium. Cells were fed fresh daily and passaged weekly. The proportion of expansion medium was increased by 20% approximately every 2 days until the cells were completely weaned, and then grown until they had been passaged 6 more times.

FIG. 6 shows colonies of hES cell at the end of 6 passages (sufficient for full adaptation) in the following media: (A) mEF conditioned medium+bFGF (8 ng/mL); (B) X-VIVO™ 10+bFGF (40 ng/mL); (C) X-VIVO™ 10+bFGF (40 ng/mL)+stem cell factor (SCF, Steel factor) (15 ng/mL); (D) X-VIVO™ 10+bFGF (40 ng/mL)+Flt3 ligand (75 ng/mL); (E) QBSF™-60+bFGF (40 ng/mL).

The following table shows the average total cell expansion per passage, for undifferentiated hES cells cultured for 4 passages in mEF conditioned medium, or for 7 passages in X-VIVO™ 10 or QBSF™-60.

TABLE 2

Growth Rates for ES Cell Cultures

| Medium | Average Cell Expansion per Passage |
| --- | --- |
| mEF conditioned medium | 2.2 fold |
| X-VIVO ™ 10 + bFGF (40 ng/mL) | 6.0 fold |
| X-VIVO ™ 10 + bFGF (40 ng/mL) + SCF (15 ng/mL) | 8.2 fold |
| X-VIVO ™ 10 + bFGF (40 ng/mL) + Flt3 ligand (75 ng/mL) | 5.0 fold |
| QBSF ™-60 + bFGF (40 ng/mL) | 6.4 fold |

The average expansion of cells per passage in X-VIVO™ 10 and QBSF™-60 was greater than the cells cultured in mEF conditioned medium culture. The cells in mEF conditioned medium were passaged on average every 7 days, while the cells in X-VIVO™ 10 and QBSF™-60 were passaged on average every 5 days. Thus, the rate of expansion in unconditioned X-VIVO™ 10 or QBSF™-60 was ~3.2 to 5.2 times faster than in mEF conditioned ES medium.

FIG. 7 shows the gene expression profile of hTERT and Oct3/4. The RNA was isolated from the cells using High Pure RNA Isolation Kit (Roche Diagnostics) and evaluated by Taqman™ assay (real time RT-PCR). The gene expression in each of the test condition is plotted relative to expression in the control culture. Taking into consideration the instrument error and assay variability, differences in expression between the test and control samples are only significant if greater than 2-fold. The analysis shows expression of hTERT and Oct-3/4 decreases somewhat upon adaptation to unconditioned X-VIVO™ 10 or QBSF™-60 medium (first four bars in each set), but returns to standard levels when the cells are passaged back into mEF conditioned medium (last three bars in each set).

To confirm that cells cultured in unconditioned medium retain their pluripotency, embryoid bodies were formed and analyzed by immunocytochemistry for phenotypic markers representing each of the three germ layers. After passage 7 in expansion medium, the cells were dissociated into small clumps using 200 U/mL collagenase IV at 37° C. for 10 min, placed in suspension culture in differentiation medium (DMEM+10% FBS) for 4 days, then transferred onto poly-L-ornithine hydrobromide coated plates for a further 10 days. They were fixed in 4% paraformaldehyde, permeabilized, and labeled by immunocytochemistry.

FIG. 8 shows the results. hES cells passaged 7 times in unconditioned X-VIVO™ 10 medium stained for α-fetoprotein (representing endoderm); muscle actin (representing mesoderm), and β-tubulin III (representing ectoderm).

These results show that hES cells can be expanded in fresh (non-conditioned) media in a feeder-free environment at a rapid rate suitable for commercial production. The cells retain the morphology of undifferentiated hES cells, and can be differentiated into derivative cells representing all three germ layers.

Example 6

Culture of hES Cells in a Defined System Free of Animal-Based Products hES cells cultured in MEF-CM on Matrigel® were passaged to a fresh (non-conditioned) serum free medium: X-VIVO™ 10 supplemented with Glutamine, non-essential amino acids and β-mercaptoethanol, plus 80 ng/mL human basic FGF on Matrigel®, and then adapted to surfaces coated with human laminin. Alternatively, cryopreserved cells were directly thawed into the same medium containing 80 ng/mL hbFGF. The cells were passaged every 5-6 days using Collagenase IV.

FIG. 9 shows that cultures grown under these conditions were similar or better than cultures on Matrigel®. (A) morphology for cells grown in mEF conditioned medium; (B) morphology fin defined medium on laminin; (C) Surface marker SSEA-4 expression in mEF-CM (H1 p62) or defined medium (H1 p34+28); (D) Expression of surface marker Tra-1-60 in mEF-CM or defined medium. Culture performance in the defined medium on laminin was superior: very large ES cell colonies were observed, with colonies representing about 80% of the culture. Levels of marker expression were as follows:

TABLE 4

Marker Expression in Defined Culture Conditions

| Passage no. | Culture medium | Surface marker expression | | Relative gene expression | | |
|---|---|---|---|---|---|---|
| | | SSEA-4 | Tra-1-60 | hTERT | Oct3/4 | Cripto |
| Experiment 1: | | | | | | |
| H1p41 | Conditioned | 79% | 93% | 1.00 | 1.00 | 1.00 |
| H1p31 + 10 | Defined | 92% | 87% | 2.85 ± 0.58* | 0.74 ± 0.04 | 1.82 ± 0.62 |
| Experiment 2: | | | | | | |
| H1p44 | Conditioned | 81% | 91% | 1.00 | 1.00 | 1.00 |
| H1p34 + 11 | Defined | 77% | 84% | 1.11 ± 0.38 | 0.57 ± 0.24 | 0.76 ± 0.39 |
| Experiment 3: | | | | | | |
| H1p47 | Conditioned | 78% | 92% | 1.00 | 1.00 | 1.00 |
| H1p35 + 12 | Defined | 80% | 86% | 2.00 ± 0.15 | 0.86 ± 0.20 | 3.12 ± 0.91 |

*mean ± SD for 3 RT-PCR determinations

Expression of other markers characteristic of undifferentiated hES cells was also comparable: Measured by real-time PCR, the levels of hTERT and Cripto were the same or greater in defined medium compared with mEF-CM, while the expression of Oct 3/4 was lower by about 28% (average of three experiments).

FIG. 10 shows expression of gene products for Oct 3/4 and hTERT. Panels A and C: phase contrast images of hES cells (H1 p34+14; H1p34+11) grown in defined medium on human laminin; Panels B and D: Oct 3/4 expression of the same fields. Panel E: TRAP analysis of telomerase activity for H1 hES cells grown in defined medium on laminin.

FIG. 11 shows teratomas generated by H1 hES cells grown in completely defined culture system at p34+11 (75 days). Panel A: Pigmented epithelium (endoderm); Panel B: Renal tissue (endoderm); Panel C: Mesenchymal tissue (mesoderm); Panel D: Neural tubes (ectoderm). All the images were taken at 200×. Tissues from three three-germ layers were observed, confirming that the cells retain their pluripotency.

One of the virtues of the culture medium described in this example is that hES cells previously grown in other conditions typically do not need to be weaned or adapted into the new system. For example, hES cells cultured in mEF-conditioned medium and cryopreserved can be directly cultured in a medium supplemented with Glutamine, non-essential amino acids, plus 80 ng/mL human basic FGF.

The compositions and procedures described above can be effectively modified without departing from the claimed invention.

The invention claimed is:

1. A method of evaluating a media for culturing human embryonic stem (hES) cells in vitro to determine if they proliferate without differentiating, comprising culturing hES cells on an extracellular matrix and in a medium comprising:
   an isotonic buffer;
   a protein nutrient, comprising serum, serum replacement, albumin, or essential and non-essential amino acids;
   lipids, fatty acids, or cholesterol, either as artificial additives or as the HDL or LDL extract of serum;
   added fibroblast growth factor at a concentration of 40 ng/mL; and
   added Flt-3 ligand at a concentration of 15 ng/ml; and
   culturing hES cells in the medium through at least four passages; and determining if the hES cells cultured in the medium have differentiated.

* * * * *